United States Patent [19]
Kasina et al.

[11] Patent Number: 6,024,937
[45] Date of Patent: *Feb. 15, 2000

[54] AROMATIC AMINE SUBSTITUTED BRIDGED NITROGEN AND SULFUR DONOR ATOM LIGANDS FOR IMAGING

[75] Inventors: Sudhakar Kasina; Eric Yau, both of Mercer Island; John M. Reno, Brier, all of Wash.

[73] Assignee: NeoRx Corporation, Seattle, Wash.

[*] Notice: This patent issued on a continued prosecution application filed under 37 CFR 1.53(d), and is subject to the twenty year patent term provisions of 35 U.S.C. 154(a)(2).

[21] Appl. No.: 08/463,232

[22] Filed: Jun. 5, 1995

Related U.S. Application Data

[63] Continuation-in-part of application No. 08/250,713, May 19, 1994, abandoned.

[30] Foreign Application Priority Data

May 18, 1995 [WO] WIPO ............... PCT/US95/06522

[51] Int. Cl.⁷ .................. A61K 51/04; C07D 39/02; C07D 213/00; C07C 319/00
[52] U.S. Cl. .................. 424/1.65; 544/322; 544/327; 544/334; 546/255; 546/261; 568/61; 568/67
[58] Field of Search .............. 534/10, 14; 564/188, 564/306; 424/1.65, 1.49, 1.69; 549/11; 544/242, 296, 297, 298, 334, 327, 322; 546/255, 261; 568/61, 67; 530/300; 548/303.7

[56] References Cited

U.S. PATENT DOCUMENTS

| | | | |
|---|---|---|---|
| 2,977,279 | 3/1961 | Kosmin | 167/22 |
| 3,027,391 | 3/1962 | Frigerio | 260/429.1 |
| 4,293,537 | 10/1981 | Wong | 424/1 |
| 4,421,735 | 12/1983 | Haber et al. | 424/1.1 |
| 4,452,774 | 6/1984 | Jones et al. | 424/1.1 |
| 4,673,562 | 6/1987 | Davison et al. | 424/1.1 |
| 4,722,892 | 2/1988 | Meares et al. | 435/7 |
| 4,732,974 | 3/1988 | Nicolotti et al. | 530/390 |
| 4,746,505 | 5/1988 | Jones et al. | 424/1.1 |
| 4,758,682 | 7/1988 | Collins et al. | 556/137 |
| 4,789,736 | 12/1988 | Canning et al. | 534/14 |
| 4,818,813 | 4/1989 | Nowotnik et al. | 534/14 |
| 4,831,122 | 5/1989 | Buchsbaum et al. | 530/389 |
| 4,861,869 | 8/1989 | Nicolotti et al. | 530/402 |
| 4,863,713 | 9/1989 | Goodwin et al. | 424/1.1 |
| 4,897,255 | 1/1990 | Fritzberg et al. | 424/1.1 |
| 4,925,650 | 5/1990 | Nosco et al. | 424/1.1 |
| 4,933,456 | 6/1990 | Rocklage et al. | 546/5 |
| 4,959,304 | 9/1990 | Simonson | 435/7 |
| 4,963,682 | 10/1990 | Bodor | 546/338 |
| 4,963,688 | 10/1990 | Bodor | 546/316 |
| 4,987,227 | 1/1991 | Burrows et al. | 540/452 |
| 5,002,754 | 3/1991 | Deutsch | 424/1.1 |
| 5,019,497 | 5/1991 | Olsson | 435/7.23 |
| 5,026,913 | 6/1991 | McBride et al. | 564/440 |
| 5,032,678 | 7/1991 | Washino et al. | 534/14 |
| 5,037,630 | 8/1991 | Fritzberg et al. | 424/1.1 |
| 5,057,301 | 10/1991 | Wilbur et al. | 424/1.1 |
| 5,059,541 | 10/1991 | Fritzberg et al. | 436/501 |
| 5,061,641 | 10/1991 | Shochat et al. | 436/545 |
| 5,071,965 | 12/1991 | Dunn et al. | 534/14 |
| 5,075,099 | 12/1991 | Srinivasan et al. | 424/1.1 |
| 5,079,346 | 1/1992 | Kung | 534/10 |
| 5,080,884 | 1/1992 | McBride et al. | 424/1.1 |
| 5,089,249 | 2/1992 | Fritzberg et al. | 424/1.1 |
| 5,091,514 | 2/1992 | Fritzberg et al. | 534/14 |
| 5,104,638 | 4/1992 | Nosco | 424/1.1 |
| 5,106,951 | 4/1992 | Morgan, Jr. et al. | 530/391.9 |
| 5,112,594 | 5/1992 | Woulfe et al. | 424/1.1 |
| 5,112,595 | 5/1992 | Woulfe et al. | 424/1.1 |
| 5,112,953 | 5/1992 | Gustavson et al. | 530/391.5 |
| 5,112,954 | 5/1992 | Abrams et al. | 530/391.9 |
| 5,120,526 | 6/1992 | Fritzberg et al. | 424/1.1 |
| 5,164,176 | 11/1992 | Gustavson et al. | 424/1.1 |
| 5,167,948 | 12/1992 | Wenzel | 424/1.1 |
| 5,169,933 | 12/1992 | Anderson et al. | 530/391.5 |
| 5,175,257 | 12/1992 | Kasina et al. | 530/391.5 |
| 5,175,343 | 12/1992 | Fritzberg et al. | 560/145 |
| 5,220,000 | 6/1993 | Theodorpulas | 534/14 |
| 5,225,181 | 7/1993 | Srivastava et al. | 424/1.1 |

(List continued on next page.)

FOREIGN PATENT DOCUMENTS

| | | | |
|---|---|---|---|
| 001812 | 5/1979 | European Pat. Off. | |
| 055 028 A1 | 6/1982 | European Pat. Off. | C08B 37/10 |
| 038 546 B1 | 2/1984 | European Pat. Off. | A61K 49/02 |
| 123307 | 10/1984 | European Pat. Off. | |
| 163 294 A2 | 12/1985 | European Pat. Off. | A61K 49/02 |
| 200 211 | 11/1986 | European Pat. Off. | |
| 237 150 A2 | 9/1987 | European Pat. Off. | C07B 59/00 |
| 317 873 A1 | 5/1989 | European Pat. Off. | C07D 207/09 |
| 351 826 A2 | 1/1990 | European Pat. Off. | C07K 13/00 |
| 432 988 A1 | 6/1991 | European Pat. Off. | C07C 323/25 |
| 2606721 | 9/1976 | Germany . | |
| 2616984 | 10/1977 | Germany . | |
| 3228503 | 2/1984 | Germany . | |
| 56-7725 | 1/1981 | Japan . | |
| 2225579 | 6/1990 | United Kingdom | C07K 7/26 |
| WO 91/17168 | 11/1991 | WIPO | C07F 5/00 |
| WO 92/07860 | 5/1992 | WIPO | C07F 13/00 |
| WO 93/15770 | 8/1993 | WIPO . | |
| WO 94/08949 | 4/1994 | WIPO | C07C 251/38 |

OTHER PUBLICATIONS

Bodor and Brewster, "Problems of Delivery of Drugs to the Brain," *Pharmacology and Therapeutics* 19(3): 337–386, 1983.

Bryson et al., "Protecting Groups in the Preparation of Thiolate Complexes of Technetium," *Inorganic Chemistry* 29(16): 2948–2951, 1990.

(List continued on next page.)

*Primary Examiner*—Jose' G. Dees
*Assistant Examiner*—Michael G. Hartley
*Attorney, Agent, or Firm*—Seed and Berry LLP

[57] ABSTRACT

The present invention provides aromatic amine substituted metal chelating compounds, chelates and chelate-targeting moiety conjugates formed from the chelating compounds, and methods for making and using these compounds. Metals capable of being chelated by the chelating compounds include radionuclides, such as $^{99m}$Tc and $^{186,188}$Re.

16 Claims, No Drawings

U.S. PATENT DOCUMENTS

| | | | |
|---|---|---|---|
| 5,242,679 | 9/1993 | Fritzberg et al. | 424/1.1 |
| 5,243,073 | 9/1993 | Neumann et al. | 564/15 |
| 5,250,666 | 10/1993 | Gustavson et al. | 530/391.5 |
| 5,252,713 | 10/1993 | Morgan, Jr. et al. | 530/391.7 |
| 5,271,927 | 12/1993 | Parker et al. | 424/9 |
| 5,279,811 | 1/1994 | Bergstein et al. | 424/1.1 |
| 5,286,848 | 2/1994 | Honzawa | 530/363 |
| 5,302,370 | 4/1994 | Neumeier et al. | 424/1.53 |
| 5,310,536 | 5/1994 | Srinivasan | 424/1.65 |
| 5,319,143 | 6/1994 | Messersmith et al. | 564/500 |
| 5,322,678 | 6/1994 | Morgan, Jr. et al. | 424/1.53 |
| 5,324,502 | 6/1994 | Green et al. | 424/1.81 |
| 5,330,737 | 7/1994 | Rajagopalan | 424/1.65 |
| 5,330,738 | 7/1994 | Nosco | 424/1.65 |
| 5,371,184 | 12/1994 | Rajagopalan et al. | 530/324 |
| 5,373,093 | 12/1994 | Vallarino et al. | 534/15 |
| 5,382,654 | 1/1995 | Lyle et al. | 530/311 |
| 5,476,644 | 12/1995 | Illig et al. | 424/1.11 |
| 5,508,458 | 4/1996 | Zhao | 556/45 |
| 5,608,110 | 3/1997 | Ramalingam et al. | 564/253 |

OTHER PUBLICATIONS

Cheesman et al., "Technetium–99m ECD: Ester–Derivatized Diamine–Dithiol Tc Complexes for Imaging Brain Perfusion," *Journal of Nuclear Medicine* 29(Suppl. 5): 788, abstract #197, 1988.

Ell, P., "Mapping Cerebral Blood Flow," *Journal of Nuclear Medicine* 33(10): 1843–1845, 1992.

Francesconi et al., "Technetium–99m N,N'–Bis(2–mercapto–2–methylpropyl)–2–aminobenzylamine: Technetium–99m Complexes of a Novel Bis(aminoethanethiol) Ligand," *J. Med. Chem.* 37: 3282–3288, 1994.

Goldstein and Betz, "The Blood–Brain Barrier," *Scientific American* 255(3): 74–83, 1986.

Holman and Devous, Sr., "Functional Brain SPECT: The Emergence of a Powerful Clinical Method," *Journal of Nuclear Medicine* 33(10): 1888–1904, 1992.

Holman et al., "Biodistribution, Dosimetry, and Clinical Evaluation of Technetium–99m Ethyl Cysteinate Dimer in Normal Subjects and in Patients with Chronic CerEbral Infarction," *Journal of Nuclear Medicine* 30(6): 1018–1024, 1989.

Ingold and Nathan, "Mechanism of, and Constitutional factors controlling, the Hydrolysis of Carboxylic Esters. Part VIII. Energies Associated with Induced Polar Effects in the Hydrolysis of Substituted Benzoic Esters," *J. Chem. Soc.*: 222–225, 1935.

Jaffé, H., "A Reexamination of the Hammett Equation," *Chem. Rev.*: 191–261, 1953.

Léveillé et al., "Intrasubject Comparison Between Technetium–99m–ECD and Technetium–99m–HMPAO in Healthy Human Subjects," *Journal of Nuclear Medicine* 33(4): 480–484, 1992.

Léveillé et al., "Characterization of Technetium–99m–L, L–ECD for Brain Perfusion Imaging, Part 2: Biodistribution and Brain Imaging in Humans," *Journal of Nuclear Medicine* 30(11): 1902–1910, 1989.

Mastrostamatis et al., "Tridentate Ligands Containing the SNS Donor Atom Set as a Novel Backbone for the Development of Technetium Brain–Imaging Agents," *J. Med. Chem.* 37: 3212–3218, 1994.

Matsuda et al., "Comparative SPECT Study of Stroke Using Tc–99m ECD, I–123 IMP, and Tc–99m HMPAO," *Clinical Nuclear Medicine* 18(9): 754–758, 1993.

Neves et al., "Neutral Technetium(II)–99m Complexes as potential Brain Perfusion Imaging Agents," *Nucl. Med. Biol.* 14(5): 503–510, 1987.

Orlandi et al., "Regional Cerebral Blood Flow and Distribution of [$^{99m}$Tc]Ethyl Cysteinate Dimer in Nonhuman Primates," *Stroke* 21(7): 1059–1063, 1990.

Taylor et al., "Technetium–99–N1–(2–Mercapto–2–Methylpropyl)–N2–(2–Propargylthio–2–Methylpropyl)–1,2–Benzenediamine (t691): Preclinical Studies of a Potential New Tracer of Regional Cerebral Perfusion," *Journal of Nuclear Medicine* 33(10): 1836–1842, 1992.

Tedjamulia et al., "Evaluation of the Brain–specific Delivery of Radioiodinated (Iodophenyl)alkyl–Substituted Amines Coupled to a Dihydropyridine Carrier," *J. Med. Chem.* 28(11): 1574–1580, 1985.

Vallabhajosula et al., "TEchnetium–99m ECD: A New Brain Imaging Agent: In Vivo Kinetics and Biodistribution Studies in Normal Human Subjects," *Journal of Nuclear Medicine* 30(5): 599–604, 1989.

Walovitch et al., "Pharmocological Characterization of Tc99m ECD in Non–Human Primates as a New Agent for Brain Perfusion Imaging," *Journal of Nuclear Medicine* 29(Suppl. 5): 788, abstract #198, 1988.

Gürsu et al., "The Reaction of N–Chloroacetylbenzamide With Some Aromatic Amines and Sysnthesis of Some Quaternary Pyridinium Compounds," *J. Fac. Pharm. Istanbul* 17:119–134, 1981.

Milligan et al., "Colorimetric Determination of Calcium Using Reagents of the Glyoxal Bis(2–hydroxyanil) Class," *Analytical Chemistry* 44(11):1822–1829, 1972.

AROMATIC AMINE SUBSTITUTED BRIDGED NITROGEN AND SULFUR DONOR ATOM LIGANDS FOR IMAGING

CROSS-REFERENCE TO RELATED APPLICATION

This application is a continuation-in-part of U.S. patent application Ser. No. 08/250,713, filed May 19, 1994, abandoned.

TECHNICAL FIELD

The present invention relates generally to chelating compounds, chelates, radiolabeled targeting moieties formed therefrom, and methods of making and using these compounds for diagnostic and therapeutic purposes. This invention is more particularly related to compounds in which the chelating atoms (e.g., nitrogen and/or sulfur) are directly attached to aromatic rings.

BACKGROUND OF THE INVENTION

Radiolabeled chelating compounds have been studied and used as pharmaceuticals for diagnostic and therapeutic purposes for a number of years. Criteria for a radiopharmaceutical include sufficient uptake of the labeled compound by a target organ or tissue and adequate retention in the target site to allow detection or therapy. A representative organ of interest is the brain. Imaging agents and therapeutic agents for the brain have typically been unsuitable due to insufficient uptake and/or inadequate retention by the brain.

Thus, there is a need in the art for improved brain imaging and therapeutic agents. The present invention fulfills this need and further provides other related advantages.

SUMMARY OF THE INVENTION

Briefly stated, the present invention in one aspect provides a compound having the formula:

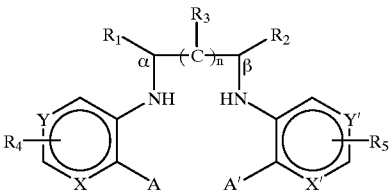

wherein:

n=0 or 1;

$R_1$ and $R_2$ are independently selected from hydrogen, =O with the proviso that both are not =O, $-(CH_2)_m Z$ where m is 0–10 and Z represents a conjugation group or targeting moiety, and $-(CH_2)_m W$ where m is 0–10 and W represents a hydrolyzable group, or $R_1$ and $R_2$ are taken together to form a cyclic anhydride or a benzene ring;

$R_3$ is hydrogen, lower alkyl, substituted lower alkyl, alkoxy, perhaloalkyl, halogen, hydroxyl, nitro, $-(CH_2)_m Z$, and $-(CH_2)_m W$;

$R_4$ and $R_5$ are attached at one or more of the ring positions and are independently selected from hydrogen, lower alkyl, substituted lower alkyl, alkoxy, perhaloalkyl, halogen, hydroxyl, nitro, $-(CH_2)_m Z$, and $-(CH_2)_m W$;

A and A' are independently selected from nitrogen, oxygen and sulfur, where a sulfur may bear a hydrogen or a sulfur protecting group, or where A and A' are both sulfur, A and A' may be joined together by a bond, where an oxygen may bear a hydrogen, and where a nitrogen may bear a hydrogen, a hydroxyl or a lower alkyl substituent, or where A and A' are both nitrogen, A and A' may be joined by $-CH_2-(CH_2)_n-CH_2-$ where n is 0 or 1;

X, Y, X' and Y' are independently selected from carbon and nitrogen;

α and β represent carbon atoms which may bear a carbon-nitrogen double bond; and wherein the compound has at least one Z or W.

In another aspect, the invention provides a preferred metal chelate compound having the formula:

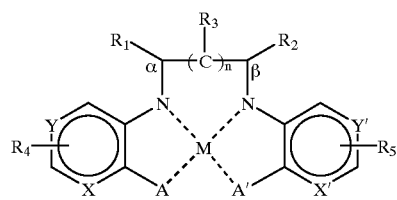

wherein:

M is a radionuclide metal or an oxide or a nitride thereof selected from the group consisting of technetium, copper, rhenium, lead, bismuth, ruthenium, rhodium, gold and palladium;

n=0 or 1;

$R_1$ and $R_2$ are independently selected from hydrogen, =O with the proviso that both are not =O, $-(CH_2)_m Z$ where m is 0–10 and Z represents a conjugation group or targeting moiety, and $-(CH_2)_m W$ where m is 0–10 and W represents a hydrolyzable group, or $R_1$ and $R_2$ are taken together to form a cyclic anhydride or a benzene ring;

$R_3$ is hydrogen, lower alkyl, substituted lower alkyl, alkoxy, perhaloalkyl, halogen, hydroxyl, nitro, $-(CH_2)_m Z$, and $-(CH_2)_m W$;

$R_4$ and $R_5$ are attached at one or more of the ring positions and are independently selected from hydrogen, lower alkyl, substituted lower alkyl, alkoxy, perhaloalkyl, halogen, hydroxyl, nitro, $-(CH_2)_m Z$, and $-(CH_2)_m W$;

A and A' are independently selected from nitrogen, oxygen and sulfur, where a nitrogen may bear a hydrogen, a hydroxyl or a lower alkyl substituent, or where A and A' are both nitrogen, A and A' may be joined by $-CH_2-(CH_2)_n-CH_2-$ where n is 0 or 1;

X, Y, X' and Y' are independently selected from carbon and nitrogen;

α and β represent carbon atoms which may bear a carbon-nitrogen double bond; and wherein the compound has at least one Z or W.

Yet another aspect of the invention provides for use of the chelate compounds described above in methods for diagnostic and therapeutic purposes. A diagnostic method is described for detecting the presence or absence of a target site within a mammalian host. This method comprises providing to cells a diagnostically effective dose of a compound of the present invention which contains a metal radionuclide, such as $^{99m}Tc$, and detecting the biodistribution of the radionuclide. A therapeutic method is described for delivering a radionuclide, such as $^{186}Re$ or $^{188}Re$, to a target site within a mammalian host. This method comprises providing to cells a therapeutically effective dose of a chelate compound of the present invention.

Other aspects of the invention will become evident upon reference to the following detailed description.

DETAILED DESCRIPTION OF THE INVENTION

Prior to setting forth the invention, it may be helpful to an understanding thereof to set forth definitions of certain terms to be used hereinafter.

Targeting moiety—is any molecule that binds to a defined population of cells. The targeting moiety may bind a receptor, an oligonucleotide, an enzymatic substrate, an antigenic determinant, or other binding site present on or in the target cell population. For example, a protein may be a targeting moiety. Antibody is used throughout the specification as a prototypical example of a targeting moiety, and tumor is used as a prototypical example of a target.

Protein—as used herein, includes proteins, polypeptides and peptides; and may be an intact molecule, a fragment thereof, or a functional equivalent thereof; and may be genetically engineered.

Antibody—as used herein, includes both polyclonal and monoclonal antibodies; and may be an intact molecule, a fragment thereof, or a functional equivalent thereof; and may be genetically engineered; examples of antibody fragments include $F(ab')_2$, Fab', Fab and Fv.

The present invention provides chelating compounds and radionuclide metal chelate compounds (complexes) prepared therefrom, as well as radiolabeled targeting moieties having the chelating compounds or chelates attached thereto. The radionuclide metal chelates of the present invention may be attached to targeting moieties, such as antibodies, to form radiolabeled targeting moieties having diagnostic and therapeutic use. Alternatively, the radionuclide metal chelates of the present invention may be used for diagnostic and therapeutic purposes without attachment to targeting moieties.

The present invention provides compounds that have a variety of uses, including as brain and heart imaging agents. The compounds are capable of rapidly complexing a metal as well as forming a stable metal chelate (complex). The presence of nitrogen atoms within the chelating compound accelerates complex formation with the metal. This acceleration is due in part to the fact that a metal, e.g., technetium, is a soft acid, and nitrogen in the form of an amine or amide, is a base. Amines generally provide for a greater increase in chelation rates than amides. Where sulfur atoms are additionally present within the chelating compound, they also provide for an increased rate of metal complexation and contribute to the stability of the resulting chelate. The presence of phenolic hydroxyl groups within the chelating compound aid in faster kinetics of metal ion chelation. The compounds of the present invention are characterized by desirable metal complex formation kinetic properties and desirable metal-chelate retention thermodynamic properties. The compounds of the present invention have the further advantage of nitrogen atoms attached directly to aromatic rings which enhances the stability of the aromatic esters of this invention with respect to hydrolysis in the bloodstream.

The chelating compounds of the present invention have the following formula (I):

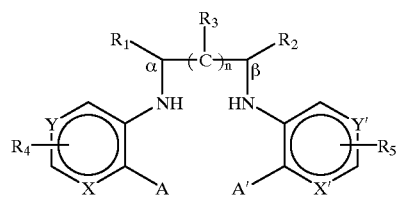

Examples of specific embodiments of the elements of the above formula include the following.

$R_1$ and $R_2$ may be independently hydrogen (H); an oxy group (=O); $-(CH_2)_m Z$ where m is 0–10 and Z represents a conjugation group or targeting moiety; or $-(CH_2)_m W$ where m is 0–10 and W represents a hydrolyzable group. Alternatively, $R_1$ and $R_2$ may be taken together to form a cyclic group, such as an anhydride or a benzene ring. A benzene ring may be benzene or benzene with one or more substituents. Examples of substituents include Cl, $CH_3$, $OCH_3$, F, Br, I, $CF_3$ and a triazene, such as $-N=N-N(CH_3)_2$. The compounds of the present invention have one or more Z and/or W groups. For example, a compound may have one Z or one W or both. Alternatively, for example, a compound may have multiple Z and/or multiple W groups.

As noted above, Z represents a conjugation group or a targeting moiety. A "conjugation group" in the compounds of the present invention is any chemically reactive group capable of forming a covalent bond with a targeting moiety under conditions that do not adversely affect the targeting moiety's functional properties. For example, where the targeting moiety is a protein such as an antibody, the conjugation group is sufficiently reactive with a functional group on the protein so that the reaction can be conducted in substantially aqueous solutions and does not have to be forced (e.g., by heating to high temperatures which may denature the protein). A conjugation group may be strongly electrophilic or nucleophilic and thereby capable of reacting directly with a targeting moiety. A precursor to a conjugation group may be a weaker electrophile or nucleophile that requires activation prior to conjugation with a targeting moiety. Conversion of a group from a precursor group to a conjugation group is generally performed in a separate step prior to conjugation with a targeting moiety. However, where a targeting moiety is unreactive with the conversion reagents and unaffected by the reaction conditions, it is possible to generate a conjugation group in the presence of the targeting moiety.

An electrophilic conjugation group may react directly with a nucleophile, either through nucleophilic substitution or nucleophilic addition. In the present invention, electrophilic conjugation groups react with the targeting moiety acting as the nucleophile. A targeting moiety may naturally possess nucleophilic group(s). For example, a targeting moiety may contain an amino group or a sulfhydryl group. Alternatively, a targeting moiety may have been modified to contain nucleophilic group(s). Procedures for modifying molecules to contain nucleophilic groups are well known to those in the art (see, e.g., catalog of Pierce Chemical Co., Rockford, Ill., and U.S. Pat. No. 4,659,839).

Electrophilic groups which provide conjugation through nucleophilic substitution include those groups which contain substituents which are readily displaced. Such readily displaced substituents are commonly referred to as leaving groups. Leaving groups include halides which are readily displaced from alkyl halides and alpha-halo carbonyl compounds, and carboxylate and stabilized oxyanions which are readily displaced from carbonyl-containing groups such as anhydrides and active esters, respectively. For example, in addition to halide ion leaving groups such as iodide, bromide, and chloride ions, other leaving groups include carboxylate ions such as acetate and trifluoroacetate and phenolate ions such as phenolate and p-nitrophenolate. Suitable active ester groups include N-hydroxysuccinimidyl, tetrafluorophenyl, nitrophenyl, and 1-hydroxybenzotriazolyl.

Electrophilic groups which provide conjugation through nucleophilic addition include those groups which contain unsaturated carbon atoms susceptible to nucleophilic addition. Suitable electrophilic carbon species include thiocyanates, isocyanates, isothiocyanates and maleimides.

As mentioned above, a conjugation group capable of reacting directly with a targeting moiety may be prepared by conversion of a weaker electrophilic or nucleophilic group to a stronger one. For example, a carboxylic acid group is a precursor group which may be activated and converted into an active ester conjugation group capable of reaction with targeting moieties as described above. Another example of a conversion to a strong electrophilic group is deprotection of a phenylsulfonyl succinimide to provide a maleimide capable of reaction with nucleophilic targeting moieties as described above.

The conjugation group may also be a nucleophilic group, such as an amino or sulfhydryl group. Such a nucleophile is capable of reacting with an electrophilic targeting moiety, such as one that naturally possesses electrophilic group(s) or one that has been modified to include electrophilic group(s). For example, a targeting moiety may contain an active ester or a maleimide group. Alternatively, procedures for modifying molecules to contain electrophilic groups are well known to those in the art (see, e.g., catalog of Pierce Chemical Co., Rockford, Ill., and U.S. Pat. No. 4,671,958).

Alternatively, Z may be a targeting moiety rather than a conjugation group. A "targeting moiety" in the compounds of the present invention has the functional property that it binds to a defined target cell population, such as tumor cells. Preferred targeting moieties useful in this regard include antibody and antibody fragments, peptides, hormones, avidin, streptavidin, and biotin. Proteins corresponding to known cell surface receptors (including low density lipoproteins, transferrin and insulin), fibrinolytic enzymes, anti-HER2, platelet binding proteins such as annexins, avidin, streptavidin, and biological response modifiers (including interleukin, interferon, erythropoietin and colony-stimulating factor) are also preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are also useful as targeting moieties of the present invention. One targeting moiety functional equivalent is a "mimetic" compound, which is an organic chemical construct designed to mimic the proper configuration and/or orientation for targeting moiety-target cell binding. Another targeting moiety functional equivalent is a short polypeptide designated as a "minimal" polypeptide. Such a polypeptide is constructed using computer-assisted molecular modeling and mutants having altered binding affinity. Minimal polypeptides exhibit the binding affinity of the targeting moiety.

Preferred targeting moieties of the present invention are antibodies (polyclonal or monoclonal), peptides, oligonucleotides or the like. Polyclonal antibodies useful in the practice of the present invention are polyclonal (Vial and Callahan, Univ. Mich. Med. Bull. 20:284–6, 1956), affinity-purified polyclonal or fragments thereof (Chao et al., Res. Comm. in Chem. Path. & Pharm. 9:749–61, 1974).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. See, generally, Kohler and Milstein, Nature 256:495–97, 1975; Eur. J. Immunol. 6:511–19, 1976.

Human monoclonal antibodies or "humanized" murine antibody are also useful as targeting moieties in accordance with the present invention. For example, murine monoclonal antibody may be "humanized" by genetically recombining the nucleotide sequence encoding the murine Fv region (i.e., containing the antigen binding sites) or the complementarity determining regions thereof with the nucleotide sequence encoding a human constant domain region and an Fc region, e.g., in a manner similar to that disclosed in European Patent Application No. 0,411,893 A2. Some murine residues may also be retained within the human variable region framework domains to ensure proper target site binding characteristics. Humanized targeting moieties are recognized to decrease the immunoreactivity of the antibody or polypeptide in the host recipient, permitting an increase in the half-life and a reduction in the possibility of adverse immune reactions.

As mentioned above, W is a hydrolyzable group. As used herein, the term "hydrolyzable group" refers to any neutral organic group that provides a charged group upon hydrolysis. The hydrolysis may be chemical or enzymatic in nature. Examples of hydrolyzable groups include esters, imidates, and nitriles which may be hydrolyzed to carboxylic acids; and carbamates which may be hydrolyzed to amines.

Referring to the above formula, the distance by which the chelating nitrogen atoms are separated may be increased by interposing a methylene group, —$CH_2$—, between the carbon atoms bonded to the nitrogens depicted. When no methylene group is interposed, represented in the above formula where n=0, the chelating nitrogens are separated by two carbon atoms. When a methylene group is interposed, represented in the above formula where n=1, the chelating nitrogens are separated by three carbon atoms. When n=1, the interposed methylene group may be substituted with $R_3$.

$R_3$ may be hydrogen, a lower alkyl group, a substituted lower alkyl group, an alkoxy group, a perhaloalkyl group, a halogen, a hydroxyl group, a nitro group, —$(CH_2)_m$Z or —$(CH_2)_m$W. As used herein, a lower alkyl group is an alkyl group of $C_6$ or less; a substituted lower alkyl group is a lower alkyl group that bears a halogen, hydroxyl or alkoxy substituent; an alkoxy group is any alkoxy group of $C_6$ or less. Suitable halogens include fluorine, chlorine, bromine and iodine.

$R_4$ and $R_5$ may be attached at one or more of the aromatic ring positions, preferably the ring carbon atoms. $R_4$ and $R_5$ are independently selected from hydrogen, a lower alkyl group, a substituted lower alkyl group, an alkoxy group, a perhaloalkyl group, a halogen, a hydroxyl group, a nitro group, —(CH$_2$)$_m$Z or —(CH$_2$)$_m$W. For R$_4$ and R$_5$, preferred groups include lower alkyl groups such as methyl, alkoxy groups such as methoxy, and halogen groups such as fluorine. Preferred Z groups include active esters such as N-hydroxysuccinimide esters and maleimides. Preferred W groups include ester and carbamate groups, such as ethyl esters and ethyl carbamates. Preferably, such preferred alkyl groups, alkoxy groups, and ester groups are substituted at the aromatic ring carbon ortho or para to the chelating nitrogen depicted in formula I above.

A and A' may be independently selected from nitrogen, oxygen and sulfur. Where a sulfur is present, it may bear a hydrogen or a sulfur protecting group. Where A and A' are both sulfur, they may be joined together by a bond or any sulfur protecting group known in the art. Where an oxygen is present, it may bear a hydrogen. Where a nitrogen is present, it may bear a hydrogen, a hydroxyl or a lower alkyl group. Where A and A' are both nitrogen, they may be joined by a carbon bridge, —CH$_2$—(CH$_2$)$_n$—CH$_2$—. In a preferred embodiment where A and A' are both sulfur, the sulfur atoms are joined together by a bond thus forming a disulfide. In a preferred embodiment where A and A' are both nitrogen, the nitrogen atoms are joined by a carbon bridge, —CH$_2$—(CH$_2$)$_n$—CH$_2$—, where n is either 0 or 1.

The chelating compounds of the present invention may be categorized by the number and type of chelating atoms. For example, where both A and A' are nitrogen, the chelating compounds of the present invention are able to bind a metal through coordination with all four nitrogen atoms. Such a chelating compound may be referred to as an "N$_4$" compound. In another embodiment, both A and A' are sulfur, resulting in the capacity for metal chelation through two nitrogen atoms and two sulfur atoms, and thus providing an "N$_2$S$_2$" chelating compound. Alternatively, A may be nitrogen and A' may be sulfur or A may be sulfur and A' may be nitrogen. Either of these embodiments are capable of metal chelation involving three nitrogen atoms and a single sulfur atom, an "N$_3$S" chelating compound. In another embodiment, A and/or A' may be oxygen atoms (e.g., hydroxyl groups). Where both A and A' are oxygen, an "N$_2$O$_2$" chelating compound results. Other embodiments include "N$_3$O" and "N$_2$SO" chelating compounds where one of either A or A' is oxygen and the other is nitrogen or sulfur, respectively.

As noted above, the sulfur atoms of the chelating compounds may bear sulfur protecting groups. Suitable sulfur protecting groups include any of the alkyl, acyl, and aryl groups, disulfides and bunte salts known by those of ordinary skill in the art. Preferred sulfur protecting groups are those that result in the formation of thioacetal, hemithioacetal, thioketal, hemithioketal, thioester or acetamidomethyl substituent. Particularly preferred groups include p-anisylidine, acetonyl, tetrahydrylfuranyl, ethoxyethyl, tetrahydrylpyranyl, acetamidomethyl and derivatives thereof. When conjugating a chelating compound of the present invention to a targeting moiety, the protecting groups may be removed just prior to metal complexation or during the radiolabeling reaction.

An acetamidomethyl sulfur-protecting group is represented by the following formula, wherein the sulfur atom shown is a sulfur donor atom of the chelating compound:

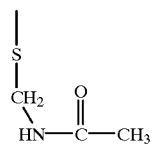

The acetamidomethyl group is displaced from the chelating compound during radiolabeling conducted at about 50° C. in a reaction mixture having a pH of about 3 to 6.

When hemithioacetal protective groups are used, each sulfur atom to be protected has a separate protective group attached to it, which together with the sulfur atom defines a hemithioacetal group. The hemithioacetal groups contain a carbon atom bonded directly (i.e., without any intervening atoms) to a sulfur atom and an oxygen atom, i.e.,

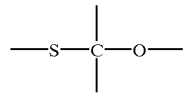

Preferred hemithioacetals generally are of the following formula, wherein the sulfur atom is a sulfur atom of the chelating compound, and a separate protecting group is attached to each of the sulfur atoms on the chelating compound:

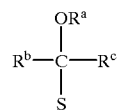

wherein R$^a$ is a lower alkyl group, preferably of from 2–5 carbon atoms, and R$^b$ is a lower alkyl group, preferably of from 1–3 carbon atoms. Alternatively, R$^a$ and R$^b$ may be taken together with the carbon atom and the oxygen atom shown in the formula to define a nonaromatic ring, preferably comprising from 3–7 carbon atoms in addition to the carbon and oxygen atoms shown in the formula. R$^c$ represents hydrogen or a lower alkyl group wherein the alkyl group preferably is of from 1–3 carbon atoms. Examples of such preferred hemithioacetals include, but are not limited to:

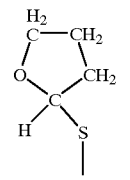

Tetrahydrofuranyl

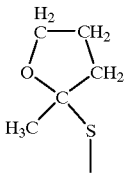

2-methyl tetrahydrofuranyl

-continued

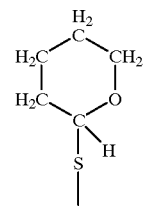

Tetrahydropyranyl

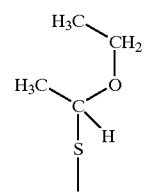

Ethoxyethyl

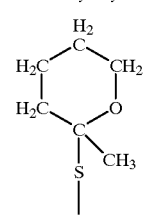

2-methyl tetrahydropyranyl

In one embodiment of the present invention, the sulfur protecting groups may join the two sulfur chelating atoms. Preferred embodiments of the sulfur protecting groups include thioketals and thioacetals, which may be prepared by condensation of the sulfur containing chelating compound with ketones and aldehydes, respectively. These particular sulfur protecting groups are represented by the following formula, wherein the sulfur atoms shown are the sulfur donor atom of the chelating compound:

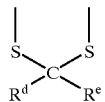

In the formula, $R^d$ and $R^e$ are independently selected from hydrogen, lower alkyl groups (preferably methyl or ethyl), lower alkoxy groups (preferably containing one or two carbon atoms), aryl groups, or taken together form a cyclic group (preferably a cyclopentane or cyclohexane ring).

These sulfur-protective groups are displaced during the radiolabeling reaction, conducted at acidic pH, in what is believed to be metal-assisted acid cleavage. Covalent bonds form between the sulfur atoms and the metal radionuclide. A separate step for removal of the sulfur-protective groups is not necessary. The radiolabeling procedure thus is simplified. In addition, the basic pH conditions and harsh conditions associated with certain known radiolabeling procedures or procedures for removal of other sulfur protective groups are avoided. Thus, base-sensitive groups on the chelating compound survive the radiolabeling step intact. Such base labile groups include any group which may be destroyed, hydrolyzed, or otherwise adversely affected by exposure to basic pH. In general, such groups include esters, maleimides, and isothiocyanates, among others. Such groups may be present on the chelating compound as conjugation groups.

The aromatic ring atoms designated as X, Y, X' and Y' are independently selected from carbon and nitrogen. Where X, Y, X' and Y' are all carbon, the aromatic rings are benzene type rings. Where X, Y, X' and Y' are all nitrogen, the aromatic rings are pyrimidine type rings. Where one of X or Y and one of X' or Y' are nitrogen, the aromatic rings are pyridine type rings. The chelating compounds and metal chelates of the present invention may also be asymmetric with respect to the nature of the aromatic rings. For example, the aromatic rings are a combination of benzene and pyridine types where X and Y are both carbon and either X' or Y' is nitrogen, or either X or Y is nitrogen and X' and Y' are both carbon. In another embodiment, the aromatic rings are a combination of benzene and pyrimidine types where X and Y are both carbon and X' and Y' are both nitrogen, or X and Y are both nitrogen and X' and Y' are both carbon. In another embodiment, the aromatic rings are a combination of pyridine and pyrimidine types where either X or Y is nitrogen and X' and Y' are both nitrogen, or X and Y are both nitrogen and either X' or Y' are nitrogen.

The carbon atoms designated $\alpha$ and $\beta$ represent carbon atoms which may bear a carbon-nitrogen double bond with the adjacent nitrogen atom. The compounds of the present invention may be symmetric and possess either no carbon-nitrogen double bonds or two carbon-nitrogen double bonds. Alternatively, the compounds may be asymmetric and possess a single carbon-nitrogen double bond, where either the carbon designated $\alpha$ or $\beta$ represents such a double bond.

As noted above, in addition to providing chelating compounds, the present invention provides radionuclide metal chelate compounds wherein a metal is chelated (complexed). The chelating compounds of the present invention rapidly form stable metal complexes (radionuclide metal chelates) when reacted with a metal.

The preferred radionuclide metal chelate compounds (complexes) of the present invention have the following formula (II):

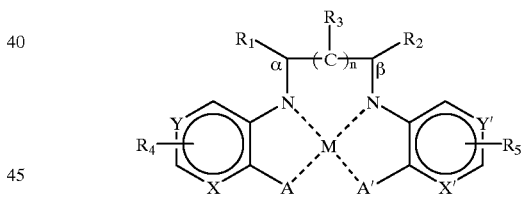

wherein $R_1-R_5$, n, X, X', Y, Y', $\alpha$ and $\beta$ are as described above. A and A' may be independently selected from nitrogen, sulfur and oxygen. M is a radionuclide metal or a radionuclide metal oxide or nitride, capable of being chelated by a compound of the present invention. Preferred metals and metal oxides include radionuclides of copper, ruthenium, technetium, rhodium, palladium, rhenium, gold, lead, and bismuth. Particularly preferred are $^{64}$Cu, $^{67}$Cu, $^{97}$Ru, $^{99m}$Tc, $^{105}$Rh, $^{109}$Pd, $^{186}$Re, $^{188}$Re, $^{198}$Au, $^{199}$Au, $^{203}$Pb, $^{212}$Pb and $^{212}$Bi.

Methods for preparing these isotopes are known. Molybdenum/technetium generators for producing $^{99m}$Tc are commercially available. Procedures for producing $^{186}$Re include the procedures described by Deutsch et al. (*Nucl. Med. Biol.* 13(4):465–477, 1986) and Vanderheyden et al. (*Inorganic Chemistry* 24:1666–1673, 1985), and methods for production of $^{188}$Re have been described by Blachot et al. (*Intl. J. of Applied Radiation and Isotopes* 20:467–470, 1969) and by Klofutar et al. (*J. of Radioanalytical Chem.* 5:3–10, 1970). Production of $^{109}$Pd is described in Fawwaz et al. (*J. Nucl. Med.* 25:786, 1984). Production of $^{212}$Pb and $^{212}$Bi is described in Gansow et al. (*Amer. Chem. Soc. Symp. Ser* 241:215–217, 1984) and Kozah et al. (*Proc. Natl. Acad. Sci. USA* 83:474–478, 1986). $^{99m}$Tc is preferred for diagnostic use, and the other radionuclides listed above have therapeutic use.

In one embodiment of the present invention, chelating compounds of the invention including acetamidomethyl and/or hemithioacetal sulfur protective groups are radiolabeled with a metal radionuclide by reacting the compound with the radionuclide under conditions of acidic pH. It is believed that the acidic pH and the presence of the metal both contribute to the displacement of the sulfur protective groups from the chelating compound. The radionuclide is in chelatable form when reacted with the chelating compounds of the invention.

In the case of technetium and rhenium, being in "chelatable form" generally requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known. (See, for example, U.S. Pat. Nos. 4,440,738; 4,434,151; and 4,652,440.) such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}$TcO$_4^{-1}$ which is in the +7 oxidation level) or sodium perrhenate (i.e., $^{188}$ReO$_4^{-1}$, $^{186}$ReO$_4^{-1}$) may be combined simultaneously with a reducing agent and a chelating compound of the invention in accordance with the radiolabeling method of the invention, to form a chelate.

Preferably, the radionuclide is treated with a reducing agent and a complexing agent to form an intermediate complex (i.e., an "exchange complex"). Complexing agents are compounds which bind the radionuclide more weakly than do the chelate compounds of the invention, and may be weak chelators. Any of the suitable known complexing agents may be used, including but not limited to, gluconic acid, glucoheptonic acid, methylene disphosphonate, glyceric acid, glycolic acid, mannitol, oxalic acid, malonic acid, succinic acid, bicine, N,N'-bis(2-hydroxy ethyl) ethylene diamine, citric acid, ascorbic acid and gentisic acid. Good results are obtained using gluconic acid or glucoheptonic acid as the Tc-complexing agent and citric acid for rhenium. When the radionuclide in the form of such an exchange complex is reacted with the chelating compounds of the invention, the radionuclide will transfer to the chelating compounds, which bind the radionuclide more strongly to form chelates of the invention. In some instances, heating is necessary to promote transfer of the radionuclide. Radionuclides in the form of such complexes also are considered to be in "chelatable form" for the purposes of the present invention.

Chelates of $^{212}$Pb, $^{212}$Bi, and $^{109}$Pd may be prepared by combining the appropriate salt of the radionuclide with the chelating compound and incubating the reaction mixture at room temperature or at higher temperatures. It is not necessary to treat the lead, bismuth, palladium, and copper radioisotopes with a reducing agent prior to chelation, as such isotopes are already in an oxidation state suitable for chelation (i.e., in chelatable form). The specific radiolabeling reaction conditions may vary somewhat according to the particular radionuclide and chelating compound involved.

In another embodiment of the present invention, where the sulfurs are protected by formation of a disulfide bond, chelating compounds of the invention are radiolabeled following reduction of the disulfide bond under mild conditions. For example, the disulfide may be reduced with SnCl$_2$ under conditions which do not reduce disulfides on proteins such as antibodies.

The chelating compounds and metal chelates of the present invention have a variety of uses, although certain uses are preferred depending upon the particular embodiment. In one aspect of the present invention, the chelating compounds and the radionuclide metal chelates are either reactive with a targeting moiety, or are conjugated to a targeting moiety. These compounds may be generally represented by the above-described compounds which bear the group Z. A chelating compound or a metal chelate that is reactive with a targeting moiety bears at least one conjugation group Z. Such conjugation groups include those described above (e.g., an active ester or a maleimide). Alternatively, the chelating compound or metal chelate may be conjugated to a targeting moiety Z. Such targeting moieties include those described above (e.g., proteins such as antibodies). The preparation of representative chelating compounds that are reactive with targeting moieties is presented in the examples below. The preparation of representative radionuclide metal-targeting moiety conjugates is also presented in the examples below. In the practice of the present invention, metal chelate-targeting moiety conjugates may be prepared by complexation of the radionuclide metal either before or after the chelating compound is conjugated to the targeting moiety. More specifically, a conjugate may be "pre-formed" or "post-formed," depending upon whether the chelating compound and targeting moiety are joined after or before the complexation of the radionuclide metal. A pre-formed conjugate comprises a chelating compound of the present invention that is first labeled with a radionuclide metal and then is conjugated to a targeting moiety. A post-formed conjugate comprises a chelating compound of the present invention that is first conjugated to a targeting moiety and then is labeled with a radionuclide metal. Thus, for pre-formed conjugates, the radionuclide is added to the chelating compound prior to the addition of the targeting moiety, whereas, for post-formed conjugates, the radionuclide is added after the addition of the targeting moiety. The final conjugate is the same regardless of how formed.

Generally, the chelating compounds of the present invention that are either reactive with targeting moieties or are conjugated to targeting moieties may be represented by the formula (I) above, where the specific embodiments of the elements of the formula include the following.

$R_1$ and $R_2$ may be independently hydrogen (H), an oxy group (=O); -(CH$_2$)$_m$Z where m is 0–10 and Z represents a conjugation group or targeting moiety; or $R_1$ and $R_2$ may be taken together to form a cyclic anhydride or a benzene ring.

The distance between the chelating nitrogen atoms of formula (I) may be varied by the imposition of a methylene group. When imposed, the methylene group may be substituted with $R_3$.

$R_3$ may be hydrogen, a lower alkyl group, a substituted lower alkyl group, an alkoxy group, a perhaloalkyl group, a halogen, a hydroxyl group, a nitro group, or -(CH$_2$)$_m$Z.

$R_4$ and $R_5$ may be attached at one or more of the aromatic ring positions, preferably the ring carbon atoms, and are independently selected from hydrogen, a lower alkyl group, a substituted lower alkyl group, an alkoxy group, a perhaloalkyl group, a halogen, a hydroxyl group, a nitro group, or -(CH$_2$)$_m$Z.

The chelating compounds reactive with or conjugated to targeting moieties have at least one Z, but may contain more than one Z. For example, any two groups selected from $R_1$–$R_5$ may be Z.

A, A', X, X', Y, Y', α, β, and n are as described above for formula (I).

Similarly, the radionuclide metal chelate compounds of the present invention that are either reactive with targeting moieties or are conjugated to targeting moieties may be represented by the formula (II). The specific embodiments of those elements of the formula denoted by $R_1$–$R_5$, n, X, X', Y, Y', α and β are as described immediately above for the chelating compounds. M is a radionuclide, radionuclide metal oxide or radionuclide metal nitride. The metal chelate compounds reactive with or conjugated to targeting moieties have at least one Z, but may contain more than one Z.

In a preferred embodiment, the compounds of the present invention are "$N_2S_2$" chelating compounds and metal chelates. Therefore, for preferred chelating compounds and metal chelates, A and A' are sulfur. For particularly preferred chelating compounds, A and A' are sulfur atoms joined together by a bond, i.e., the chelating compounds are disulfides. Preferred compounds of the present invention have X, Y, X' and Y' as carbon. For the metal chelates of the present invention, technetium (e.g., $^{99m}$Tc) is a preferred metal for diagnostic purposes, and rhenium (e.g., $^{186}$Re and $^{188}$Re) is a preferred metal for therapeutic purposes.

Further, in a preferred embodiment, the compounds of the present invention, which are reactive with targeting moieties, possess a single conjugation group. A preferred conjugation group is the N-hydroxysuccinimide ester group.

In a preferred embodiment, in addition to the above-mentioned preferences, the conjugation group is an aromatic ring substituent, i.e., either $R_4$ or $R_5$ is –$(CH_2)_m$Z. For one such preferred embodiment, n=1, $R_1$–$R_4$ are hydrogen, and $R_5$ is –$(CH_2)_m$Z, where m=0 and Z is an active ester such as an N-hydroxysuccinimide ester. Alternatively, the conjugation group may be a substituent of the carbons linking the chelating nitrogens, i.e., $R_1$–$R_3$. In one such preferred embodiment, n=1, $R_1$ or $R_2$ is –$(CH_2)_m$Z where m=0 and Z is an N-hydroxysuccinimide ester, $R_3$ is hydrogen, and $R_4$ and $R_5$ are methyl. In another such preferred embodiment, n=1, $R_1$ and $R_2$ are hydrogen, $R_3$ is –$(CH_2)_m$Z as described immediately above, and $R_4$ and $R_5$ are methyl.

In another preferred embodiment, the conjugation group is an anhydride, i.e., $R_1$ and $R_2$ are taken together to form a cyclic anhydride. In one such embodiment, in addition to the above-mentioned preferences, $R_1$ and $R_2$ are taken together to form a cyclic anhydride, n=0, and $R_4$ and $R_5$ are fluorine.

For the compounds of the present invention which are conjugated to targeting moieties, preferred targeting moieties include proteins such as antibodies and binding proteins such as avidin and streptavidin.

In another aspect of the present invention, the chelating compounds and the radionuclide metal chelate compounds are used in radiopharmaceutical applications without the necessity for a conjugation group or targeting moiety. Such chelating and metal chelate compounds are useful by virtue of their lipophilic properties and may be generally represented by the above-described compounds which bear hydrolyzable group W.

Generally, the chelating compounds of the present invention that are useful without possessing a conjugating group or targeting moiety may be represented by the formula (I) above where the specific embodiments of the elements of the formula include the following.

$R_1$ and $R_2$ may be independently hydrogen (H), an oxy group (=O); or –$(CH_2)_m$W where W represents a hydrolyzable group; or $R_1$ and $R_2$ may be taken together to form a cyclic anhydride or a benzene ring.

The distance between the chelating nitrogen atoms of formula (I) may be varied the imposition of a methylene group, —$CH_2$. When imposed, the methylene group may be substituted with $R_3$.

$R_3$ may be hydrogen, a lower alkyl group, a substituted lower alkyl group, an alkoxy group, a perhaloalkyl group, a halogen, a hydroxyl group, a nitro group, or –$(CH_2)_m$W.

$R_4$ and $R_5$ may be attached at one or more of the aromatic ring positions, preferably the ring carbon atoms, and are independently selected from hydrogen, a lower alkyl group, a substituted lower alkyl group, an alkoxy group, a perhaloalkyl group, a halogen, a hydroxyl group, a nitro group, or –$(CH_2)_m$W.

The chelating compounds that are useful in the absence of a conjugation group or targeting moiety have at least one W, but may contain more than one W. For example, any two groups selected from $R_1$–$R_5$ may be W.

A, A', X, X', Y, Y', α, β, and n are as described above for formula (I).

Similarly, the radionuclide metal chelate compounds of the present invention that are useful without a conjugation group or targeting moiety may be represented by the formula (II) where the specific embodiments of the elements of the formula, $R_1$–$R_5$, n, X, X', Y, Y', α and β are as described immediately above for the chelating compounds. M is a radionuclide, radionuclide metal oxide or radionuclide metal nitride. The metal chelates that are useful in the absence of a conjugation group or targeting moiety have at least one W, but may contain more than one W.

In a preferred embodiment, W is an enzyme hydrolyzable group, such as an ester or a carbamate. Such groups are subject to hydrolysis by esterases commonly found in tissues such as the heart and brain. In a particularly preferred embodiment, the hydrolyzable group is an ethyl ester or ethyl carbamate.

Preferred embodiments of the compounds which possess hydrolyzable groups W include the preferences for M, A, A', X, Y, X' and Y' described above for the compounds which possess a conjugation group or a targeting moiety, Z. In a preferred embodiment, the compounds of the present invention having hydrolyzable groups W possess more than one W.

In one preferred embodiment, in addition to the above-mentioned preferences, the hydrolyzable group is an aromatic ring substituent, i.e., $R_4$ and $R_5$ are –$(CH_2)_m$W. For one such embodiment, n=1, $R_1$–$R_3$ are hydrogen, and $R_4$ and $R_5$ are –$(CH_2)_m$W, where m=0 and W is either an ester (i.e., —$CO_2$Et), a carbamate (i.e., —NH—$CO_2$Et) or a nitrile (—CN). Alternatively, in another preferred embodiment, where both $R_4$ and $R_5$ are —$(CH_2)_m$—W as described immediately above, n=1, either $R_1$ or $R_2$ is an oxy group (=O) and $R_3$ is either hydrogen or –$(CH_2)_m$W.

In another preferred embodiment, the hydrolyzable group W is a substituent of the carbon atoms linking the chelating nitrogens, i.e., one or more of $R_1$–$R_3$ is –$(CH_2)_m$W. For example, in one such preferred embodiment, in addition to the above noted preferences, n=0, $R_1$ and $R_2$ are –$(CH_2)_m$W where m=0 and W is an ester, and $R_4$ and $R_5$ are fluorine. In another such preferred embodiment, n=1, either $R_1$ or $R_2$ is an oxy group (=O), $R_3$ is –$(CH_2)_m$W as described immediately above, and $R_4$ and $R_5$ are methyl. In a further such preferred embodiment, n=1, $R_1$ and $R_2$ are hydrogen, $R_3$ is –$(CH_2)_m$W as described above, and $R_4$ and $R_5$ are methoxy.

The lipophilic properties of these chelating and metal chelate compounds are due in part to the hydrophobic nature of hydrolyzable W. As noted above, W includes any neutral organic group that provides a charged group upon hydrolysis. Generally, the neutral organic group of W is hydrophobic and imparts lipophilic character to the chelating and metal chelate compounds.

The lipophilic compounds of the present invention are particularly useful in vivo where it is desirous to accumulate the metal chelates in tissues such as the brain and heart. In such applications, the administered lipophilic metal chelates reach these tissues through the bloodstream and, because of their lipophilic properties, the metal chelates are absorbed by these tissues. Once absorbed into the tissues, the metal chelates are subject to hydrolysis where the hydrolyzable group, W (e.g., an ester), which imparted lipophilicity to the chelate is converted to a charged species (e.g., an acid if the ester is a carboxylate ester, and a base if the ester is a carbamate ester) and is thereby prevented from escaping the tissue.

Suitable hydrolyzable groups W included nitriles, carbamates, and esters. Preferred hydrolyzable groups include carbamates and carboxylate esters. Preferred carboxylate esters include methyl, ethyl, propyl and isopropyl esters. Preferred carbamate esters include methyl and ethyl esters.

The lipophilic metal chelates of the present invention, which bear hydrolyzable groups W, may undergo either chemical or enzymatic hydrolysis to yield residually charged metal chelates. To be effective, the metal chelates are resistant to rapid hydrolysis in the bloodstream, but are readily hydrolyzed upon uptake by the tissue of interest. Hydrolysis which occurs in the bloodstream is primarily chemical in nature while tissue hydrolysis is primarily enzymatic. Because the majority of the uptake of the compound by the brain or heart occurs in the first pass or two through the blood stream, a compound of the present invention need typically only be stable to serum hydrolysis for less than about 1 hour.

In one embodiment, the compounds of the present invention are additionally resistant toward chemical hydrolysis. For example, the chelating compounds and metal chelates that bear ester groups, which are directly conjugated to the aromatic ring as either ortho or para substituents relative to the chelating nitrogen, are particularly stable toward chemical hydrolysis. Referring to the above formulas, these preferred compounds are represented by those compounds where $R_4$ and/or $R_5$ are $-(CH_2)_m W$ (m=0 and W is an ester), and where $R_4$ and/or $R_5$ is located ortho or para to the chelating nitrogen.

Such suitably substituted esters are resistant toward chemical hydrolysis by virtue of electron donation from the chelating nitrogen through the aromatic ring to the ester carbonyl group. This dispersal of electron density renders the ester carbonyl relatively electron rich and reduces its reactivity as an electrophile. Because the rate-determining step in ester hydrolysis is the addition of a nucleophilic water molecule to the ester carbonyl, ester carbonyl groups that are less electrophilic react more slowly toward nucleophilic addition. Thus, ester carbonyl groups which are stabilized toward nucleophilic addition by electron donating groups are resistant toward hydrolysis. For these reasons, the above-described esters of the present invention are resistant toward chemical hydrolysis in the bloodstream.

While the efficacy of the administration of the lipophilic compounds of the present invention resides in part in their stability toward hydrolysis in the bloodstream, their ultimate utility as radiopharmaceutical agents relies on their capacity to be taken up and retained by specific tissues. The uptake of these compounds into the tissue results from the particular character of the compounds and the permeability of the tissues toward such compounds.

The compounds of the present invention are retained within a tissue, such as brain, by conversion of the lipophilic compounds to charged compounds (ionic species) by hydrolysis. The compounds of the present invention, which are resistant to chemical hydrolysis, are readily susceptible to enzymatic hydrolysis. Suitable hydrolyzable groups that are converted to charged compounds by enzymatic action include ester and carbamate groups which are converted to carboxylic acid and amino groups, respectively.

The compounds of the present invention may be taken up by various tissues, but are primarily intended for the heart and brain. The metal chelates of the present invention may be selectively taken up by either heart or brain tissue depending upon the nature of the chelate.

Cationic metal chelates are taken up by heart tissue. The residual positive charge of these cationic metal chelates results from chelation of the positively charged metal or metal oxide or nitride (e.g., Tc=O, +3) with a chelating compound which complexes the metal or metal oxide or nitride through only two formal negative charges. Such a chelating compound would be an "$N_2S_2$" compound as described above where both nitrogens are doubly bonded to the carbon atoms which separate the chelating nitrogen. Referring to the formulas above, both $\alpha$ and $\beta$ carbons form a double bond with the chelating nitrogens. For these metal chelates, neither nitrogen bears a formal negative charge. The overall charge of such a metal chelate is +1 by virtue of the chelating sulfur atoms each bearing single formal negative charge, thus reducing the +3 charge due to the metal species by −2 through complexation with each of the sulfur atoms. A representative synthesis of such a chelating compound and its corresponding metal chelate is presented in the examples below.

Neutral metal chelates are taken up by the brain. For these compounds, the metal chelate has no residual charge. The positive charge of the metal is neutralized by the formally negatively charged chelating compound. More specifically, for an "$N_2S_2$" chelate embodiment, the metal's +3 charge is neutralized by chelation through the two formally negatively charged sulfur atoms and one formally negatively charged nitrogen atom. Representative syntheses of neutral chelating compounds and their corresponding metal chelates are presented in the examples below. Neutral metal chelates pass across the blood brain barrier. Once inside the brain, such compounds are converted to charged species by hydrolysis of the hydrolyzable group(s) on the compounds. Upon conversion to a charged species, the compound is unable to exit the brain via the blood brain barrier and, thus, is trapped within the brain.

The radiolabeled chelates of the present invention have use in diagnostic and therapeutic procedures, both for in vitro assays and for in vivo medical procedures. The radiolabeled chelates may be delivered (e.g., administered to a warm-blooded animal such as a human) intravenously, intraperitoneally, intralymphatically, locally, or by other suitable means, depending on such factors as the type of target site. The amount to be provided will vary according to such factors as the type of radionuclide (e.g., whether it is a diagnostic or therapeutic radionuclide), the route of delivery, the type of target site(s), the affinity of the targeting moiety, if employed, for the target site of interest, and any cross-reactivity of the targeting moiety, if employed, with normal tissues. Appropriate amounts may be established by conventional procedures, and a physician skilled in the field to which this invention pertains will be able to determine a suitable amount for a patient. A diagnostically effective dosage is generally from about 5 to about 35 and typically from about 10 to about 30 mCi per 70 kg body weight. A therapeutically effective dosage is generally from about 20 mCi to about 300 mCi or higher. For diagnosis, conventional non-invasive procedures (e.g., gamma cameras) are used to detect the biodistribution of the diagnostic radionuclide, thereby determining the presence or absence of the target sites of interest (e.g., tumors, heart, brain).

The comparatively low intestinal localization of the therapeutic radiolabeled chelates of the present invention or catabolites thereof permits increased dosages, since intestinal tissues are exposed to less radiation. The clarity and accuracy of diagnostic images also is improved by the reduced localization of radiolabeled chelates or catabolites thereof in normal tissues.

The following examples are provided for purposes of illustration, not limitation.

EXAMPLES

Example 1

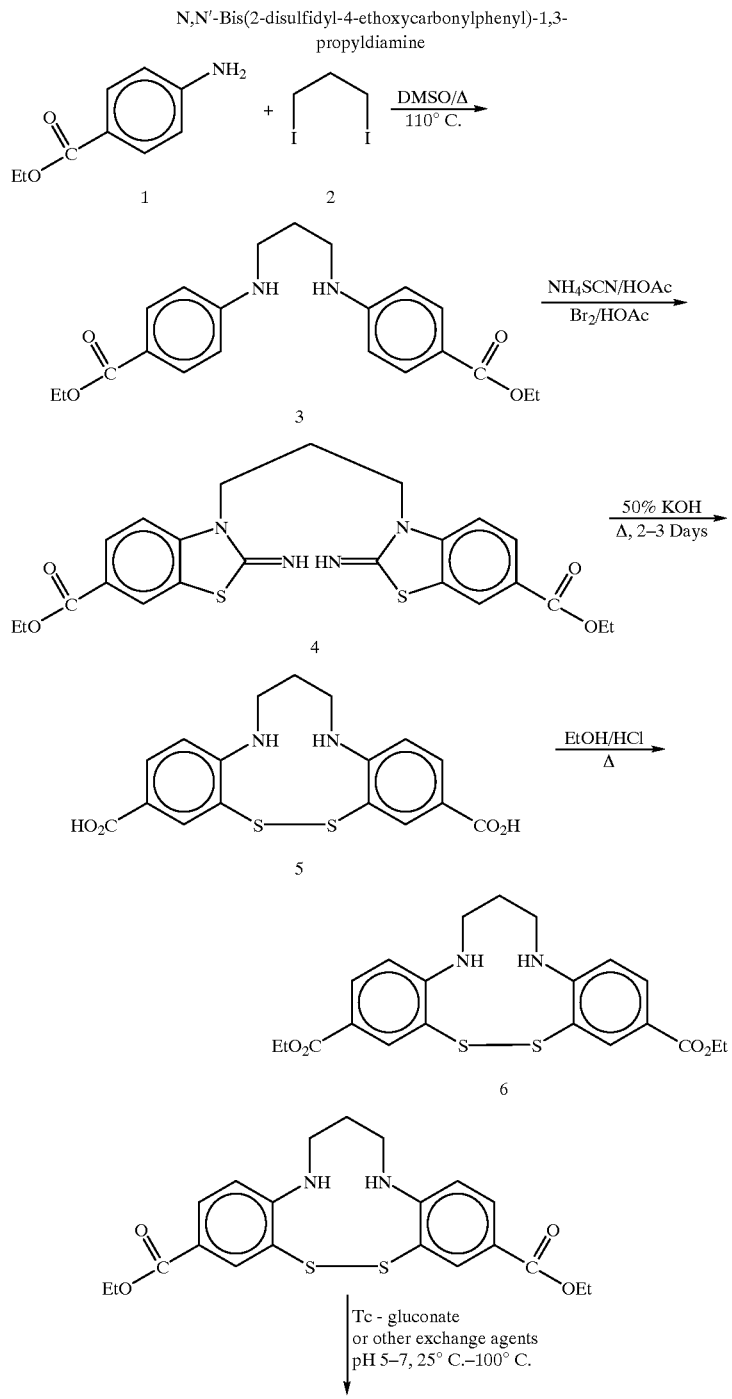

-continued

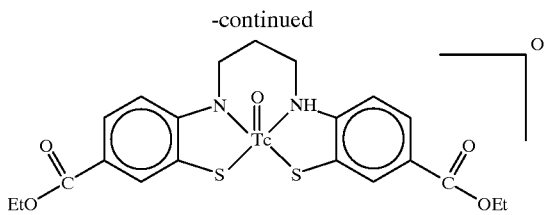

4,4-Diethoxycarbonylpropyl-1,3-dianiline 3:

A stirred solution of 2.065 g (1.25 mole) ethyl-4-amino benzoate 1, 14.35 mL (0.125 mole) 1,3-diidopropane 2 and 10.5 g (0.125 mole) sodium bicarbonate in 500 mL dry DMSO is heated at 110° C. for 3 hours under nitrogen. Upon cooling, the mixture is poured into 2 L of ice water with stirring and the resulting precipitate collected by filtration. The precipitate is then washed with glacial acetic acid (14×75 mL) until all of the starting ethyl-4-aminobenzoate has been removed. After drying in vacuo, the product, 3, thus obtained is used in the next step without further purification.
1,3-Di(2-imino-6-ethoxycarbonylbenzthiazolyl-3-)propane 4:

Ammonium thiocyanate (16.5 g, 0.217 mole) is added to a magnetically stirred suspension of 4,4-diethoxycarbonylpropyl-1,3-dianiline (prepared as described above) (10.0 g, 0.027 mole) in 1500 mL glacial acetic acid. A solution of bromine (34.6 g, 0.216 mole) in 100 mL glacial acetic acid is then added dropwise to the suspension with stirring at room temperature. After stirring the reaction mixture overnight at room temperature, the dihydrobromide salt of the crude product is collected by filtration and dried. The product, 4, is isolated by dissolving the crude product in hot water, adjusting to basic pH with the addition of saturated sodium bicarbonate solution, collecting the precipitate by filtration, and drying in vacuo.
N,N'-Bis(2-disulfidyl-4-carbonylphenyl)-1,3-propyldiamine 5:

Solid potassium hydroxide (20.0 g, 0.357 mole) is added to a suspension of the (1.0 g, 0.002 mole) 4 in 40 mL distilled water, and the resulting mixture is heated at 120° C. for 12 hours. Complete dissolution occurs after 1 hour. The reaction mixture is then cooled in an ice bath and the pH is adjusted to 5.0 with 5.0 N acetic acid. The aqueous solution is then extracted with three 100 mL portions of ethyl acetate. The combined ethyl acetate extracts are dried over anhydrous sodium sulfate and the drying agent is filtered. Removal of solvent yields the product 5.
N,N'-Bis(2-disulfidyl-4-ethoxycarbonylphenyl)-1,3-propyldiamine 6:

A magnetically stirred suspension of 5 (0.5 g, 0.0013 mole) in 200 mL absolute ethyl alcohol is saturated with dry hydrogen chloride gas. The reaction mixture is then heated under reflux for 3 days. Upon cooling, the solvent is removed under reduced pressure, to yield the product, 6, as its dihydrochloride salt. A solution of the salt in 100 mL distilled water is adjusted to pH 8.5 to 9.0 with 0.2 M sodium bicarbonate solution and the aqueous solution extracted with three 100 mL portion methylene chloride. The combined methylene chloride extracts are dried over anhydrous sodium sulfate and the drying agent filtered. Removal of the solvent under reduced pressure gives the crude product 6 which is isolated and purified by flash chromatography using silica gel and eluting with methylene chloride and ethyl acetate.
Tc-99m radiolabeling of N,N'-Bis(2-disulfidyl-4-ethoxycarbonylphenyl)-1,3-proplydiamine 6:

A solution of 0.6 mL of 170 μg/mL N,N'-bis(2-disulfidyl-4-ethoxycarbonylphenyl)-1,3-propyldiamine in either acetonitrile or isopropanol is added to 1.1 mL of Tc-99m gluconate (prepared from 0.12 mg stannous chloride dihydrate, 5.0 mg sodium gluconate at pH 6.1–6.3, and 100 mCi/mL of Tc-99m pertechnetate). The resulting mixture is incubated either at room temperature for 15–30 minutes or heated at 75° C. for 2–5 minutes followed by cooling with an ice bath. The crude reaction mixture is then diluted with 3 mL water and purified by reverse phase chromatography. The crude product is loaded onto a pre-conditioned C-18 sample preparation cartridge (SPICE cartridge supplied by Analtech) and eluted with 5 mL water followed by 10 mL 20% ethanol-saline, and 10 mL 40% ethanol saline, respectively. The Tc-99m chelate product is eluted with 10 mL 50% ethanol-saline to give 75% radiochemical yield of the desired product. The radiochemical purity of the eluent was analyzed by reverse phase C-18 isocratic liquid chromatography using 60% ethanol-saline as the mobile phase at a flow rate of 0.8 mL per minute.

Example 2

Diethyl-N,N'-bis(2-disulfidyl-4-flourophenyl)-1,2-ethane dicarboxylate

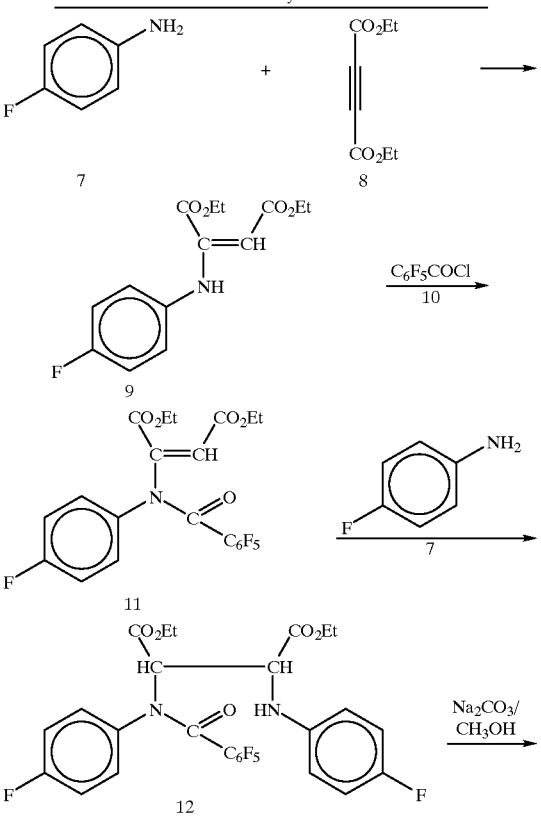

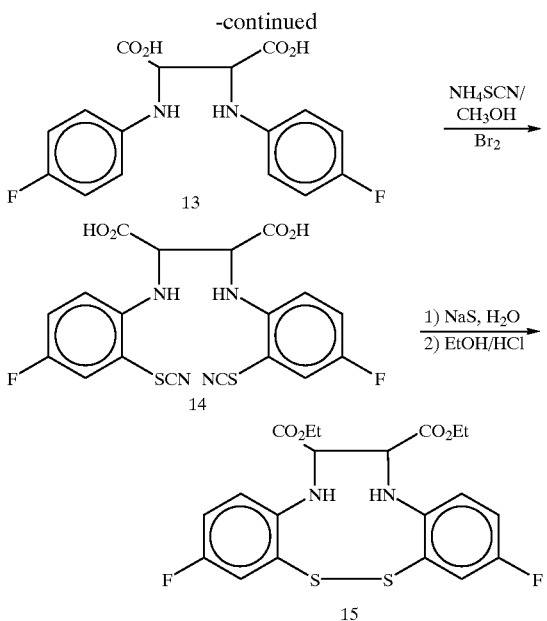

Diethyl-1 (p-fluoroanilino)ethylene dicarboxylate 9:

A solution of 10.0 g (0.09 mole) 4-fluoroaniline 7 and 8.0 g (0.047 mole) diethylacetylene dicarboxylate 8 is stirred at room temperature for 72 hours. The crude product is purified by flash chromatography using silica gel eluted initially with ethyl acetate:hexane (1:4) and finally with ethyl acetate. The fractions containing the product are combined and concentrated under reduced pressure to give 9 as a yellow oil.

Diethyl-1-(p-fluorophenyl pentafluorobenzamido)ethylene dicarboxylate 11:

To a magnetically stirred solution of 4.0 g (0.014 mole) 9 in 25 mL methylene chloride is added, 6.6 g (0.029 mole) pentafluorobenzoyl chloride 10, followed by the addition of 9.9 mL (0.07 mole) triethylamine. After 48 hours, the solvent from the reaction mixture is removed under reduced pressure and dried. To the dried residue is added 10 mL anhydrous methylene chloride and the resulting solution is filtered. The filtrate is concentrated to yield the crude product which is purified by flash chromatography using silica gel eluted initially with 40:60 ethyl acetate:hexane and finally with ethyl acetate. The fractions containing the product are combined and concentrated under reduced pressure to yield 11 as a white solid.

Diethyl-1-(p-fluorophenyl pentafluorobenzamido)-2-(p-fluoroanilino) ethane dicarboxylate 12:

To a magnetically stirred solution of 2.0 g (0.007 mole) 11 in 25 mL methylene chloride is added 1.6 g (0.014 mole) 4-fluoroaniline 7. The reaction mixture is then stirred at room temperature for 48 hours followed by removal of solvent under reduced pressure. The resulting crude product is purified by flash chromatography using silica gel eluting initially with 30:70 ethyl acetate:hexane and finally with ethyl acetate. The fractions containing the product are combined and concentrated under reduced pressure to yield 12 as a white solid.

1,2-Bis(p-fluoroanilino)ethane dicarboxylic acid 13:

To a magnetically stirred solution of 1.0 g (0.017 mole) 12 in 50 mL methanol is added 50 mL of 0.2 M sodium carbonate solution. After stirring at room temperature for 24 hours, the solvent is removed under reduced pressure. The crude product is purified by silica gel column chromatography eluting initially with 30% ethyl acetate-hexane followed by ethyl acetate. Fractions containing the product are combined and concentrated. The product is dissolved in 50 mL water, cooled, the pH is adjusted to 6.0 with 6.0 N acetic acid, and the aqueous solution is extracted with three 100 mL portions of ethyl acetate. The combined ethyl acetate extracts are dried over anhydrous sodium sulfate and filtered. Solvent from the filtrate is removed under reduced pressure to yield 13 as a white solid.

1,2-Bis(2'-thiocyano-4'-fluoroanilino)ethane dicarboxylic acid 14:

A methanolic solution of bromine is added dropwise to a magnetically stirred solution of 13 and ammonium thiocyanate in methanol. After completion of the addition, the reaction mixture is stirred overnight at room temperature. The resulting precipitate is then filtered and dried. Concentration of the filtrate under reduced pressure provides additional crude product. The combined crude product is then chromatographed on silica gel column using ethyl acetate and methylene chloride as eluting solvents. The fractions containing the product are combined and the solvent is removed under reduced pressure to yield 14.

Diethyl-N,N'-bis(2-disulfidyl-4-fluorophenyl)-1,2-ethane dicarboxylate 15:

To a magnetically stirred solution of 14 in water is added sodium disulfide and the resulting solution is heated at reflux. Upon completion of the reaction, the mixture is concentrated to dryness. The residue is then dissolved in ethanol and the resulting solution is saturated with dry hydrogen chloride gas and heated at reflux. Additional dry hydrogen chloride gas is occasionally added during the heating. Upon completion of reaction, the solvent is removed under reduced pressure to yield the crude product. The crude product is purified by silica gel chromatography eluting with ethyl acetate initially and finally with methylene chloride. The fractions containing the product are combined and concentrated to yield 15.

Incorporation of a radionuclide metal into the chelating compound may be accomplished as described above in Example 1.

Example 3

N,N'-Bis(2-disulfidyl-4-methylphenyl)-γ,γ'-diamino isovalerate N-hydroxysuccinimide

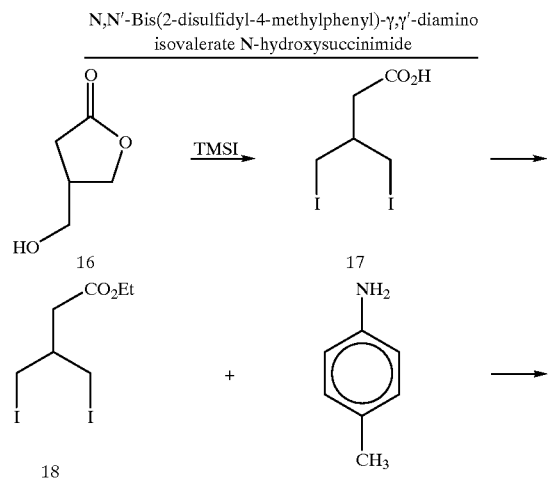

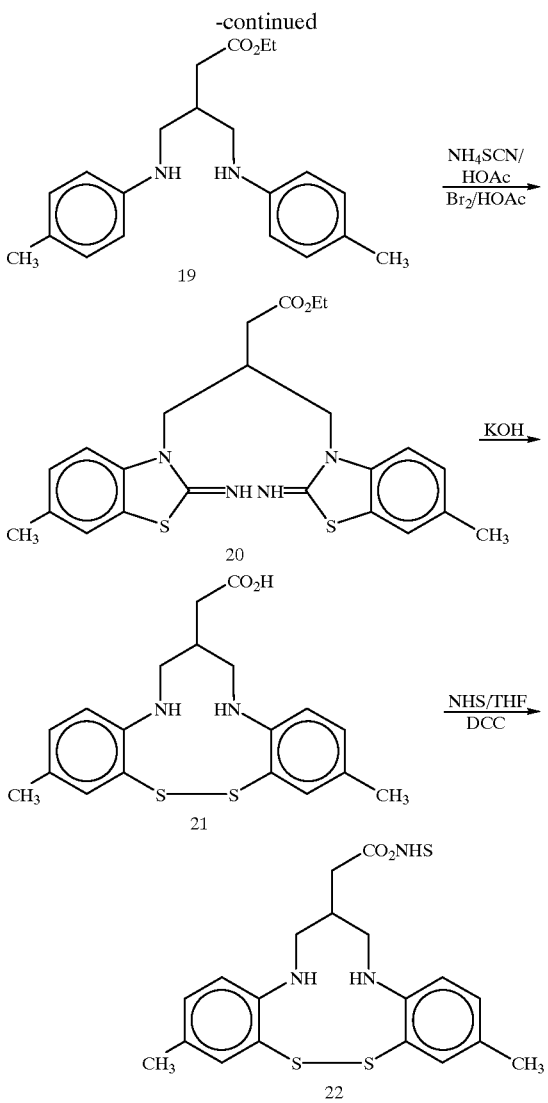

3-Iodomethyl-4-iodobutyric acid 17:

To a solution of 1.61 g (10 mmol) 3-hydroxymethyl-4-butanolide 16 (prepared by the procedure of Kinoshita and Hirano, *J. Heterocyclic Chem.* 29:1025, 1992) in 100 mL carbon tetrachloride is added 8 g (40 mmole) of iodotrimethylsilane. The reaction mixture is heated at 50° C. for 12 h under nitrogen. The mixture is diluted with chloroform and washed with water (3×100 mL), 5% aqueous sodium thiosulfate (100 mL), 10% aqueous sodium bicarbonate and brine. The organic layer is dried over magnesium sulfate, filtered and evaporated to give the desired crude product. The crude product is purified by silica gel chromatography (ethyl acetate-hexane=3:7 as the eluting solvent) to give 3-iodomethyl-4-iodobutyric acid 17.

Ethyl-3-iodomethyl-4-iodobutyrate 18:

A solution of 2.831 g (8 mmole) 3-iodomethyl-4-iodobutyric acid 17 in 80 mL ethanol is saturated with HCl gas at 0° C. After stirring the solution at room temperature for two days, the solvent is removed under vacuum and the residue is dissolved in dichloromethane. The dichloromethane layer is washed with 10% aqueous sodium bicarbonate (3×100 mL), water (1×100 mL) and brine. The separated dichloromethane layer is dried over with magnesium sulfate, filtered and evaporated to give ethyl-3-iodomethyl-4-iodobutyrate 18.

Ethyl-γ,γ'-di(4-methylanalino) isovalerate 19:

A stirred solution of 7.5 g (70 mmole) 4-toluidine, 2.674 g (7 mmole) ethyl-3-iodomethyl-4-iodobutyrate 18 and 0.588 g (7 mmole) sodium bicarbonate in 30 mL dry dimethyl sulfoxide is heated at 110° C. for 3 h under nitrogen. The cooled mixture is poured onto 400 mL ice water with stirring. The resulting precipitate is collected by filtration. The remaining 4-toluidine in the precipitate is removed by washing with aqueous acetic acid several times. The product, ethyl-γ,γ'-di(p-methylanilino)isovalerate 19, is obtained by recrystallization of the washed precipitate in heptane.

Ethyl-γ,γ'-[1,3-di(2-imino-6-methyl benzthiazolyl-3)] isovalerate 20:

To a magnetically stirred suspension of 2.0 g (6.5 mmole) ethyl-γ,γ'-di(4-methylanalino)isovalerate 19 in 250 mL glacial acetic acid is added ammonium thiocyanate (3.5 g, 0.046 mole) followed by the dropwise addition of a solution of bromine (7.27 g, 0.046 mole) in 50 mL glacial acetic acid. After the addition is complete, stirring is continued overnight. The yellow precipitate of dihydrobromide salt is filtered and dried. The dried solid is then dissolved in hot water and the benzothiazole free base is liberated with saturated sodium bicarbonate solution. The white solid is filtered and dried to give crude product 20 which is used without further purification.

N,N'-Bis(2-disulfidyl-4-methylphenyl)-γ,γ'-diaminoisovaleric acid 21:

To a suspension of 20 (1.0 g, 0.0022 mole) in 40 mL distilled water, solid potassium hydroxide pellets (20.0 g, 0.357 mole) is added and the resulting solution heated at 120° C. for 15–24 hours. After several hours of heating, the suspension becomes a clear solution. The reaction mixture is cooled in an ice bath and acidified with 5.0 N acetic acid to pH 5.0 and the aqueous solution is extracted with three 100 mL portions of ethyl acetate. The combined ethyl acetate extracts are dried over anhydrous sodium sulfate and filtered. Solvent from the filtrate is removed under reduced pressure to give 21. The crude product is chromatographed on silica gel column using 20:80 mixture of ethyl acetate-:hexane with 1% acetic acid as eluting solvent to give 21 as a crystalline yellow solid.

N,N'-Bis(2-disulfidyl-4-methylphenyl)-γ,γ'-diaminoisovalerate N-hydroxysuccinimide 22:

Compound 21 is reacted with N-hydroxysuccinimide (NHS) and dicyclohexylcarbodiimide (DCC) in either tetrahydrofuran or dimethylformamide (DMF) at room temperature. After stirring overnight at room temperature, the solvent is removed and the crude product, 22, is purified by column chromatography on silica gel.

Example 4

N,N'-Bis (2-disulfidyl-4-methoxyphenyl)γ,γ'-diaminoisovleric acid, ethyl ester

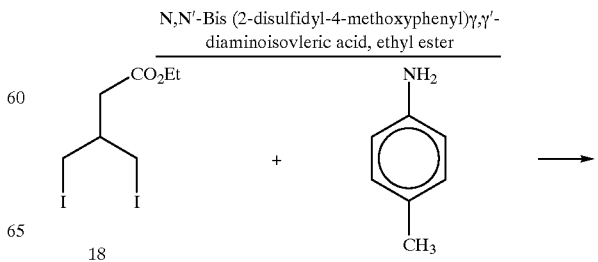

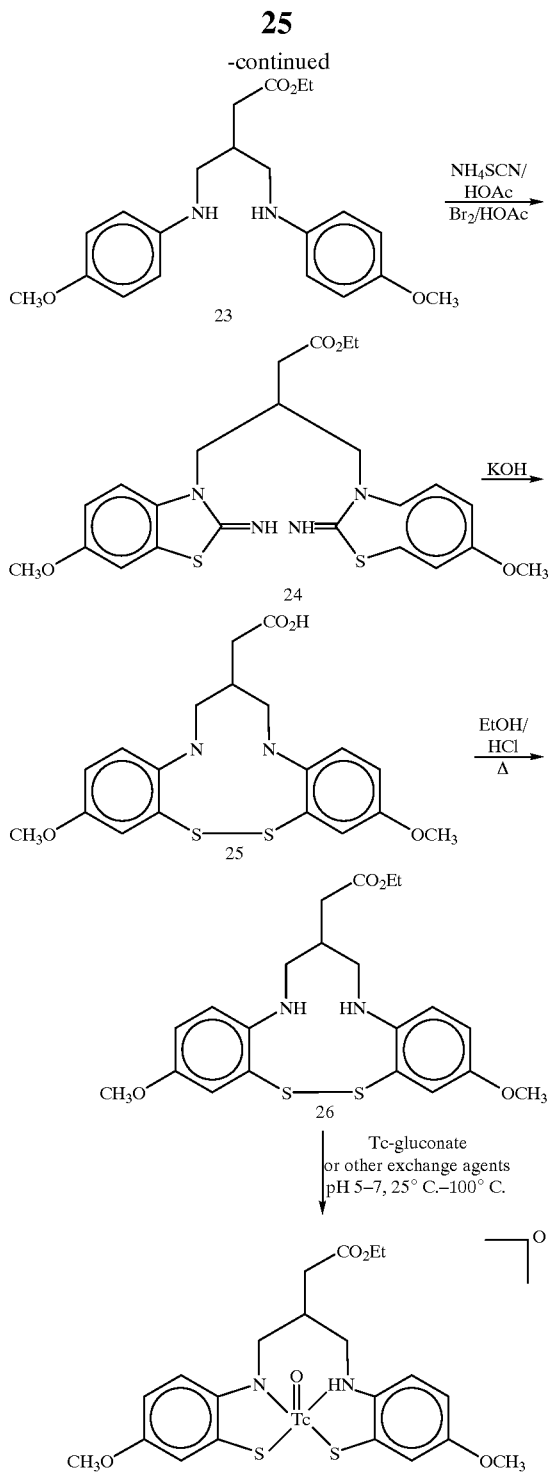

Ethyl-γ,γ'-[1,3-di(2-imino-6-methoxy benzthiazolyl-3)] isovalerate 24:

To a magnetically stirred suspension of 2.0 g (6.5 mmole) 23 in 250 mL glacial acetic acid is added (3.5 g, 0.046 mole) ammonium thiocyanate. To the stirred solution at room temperature is added dropwise a solution of bromine (7.27 g, 0.046 mole) in 50 mL glacial acetic acid. After the addition is complete, the reaction mixture is stirred overnight at room temperature. The resulting yellow precipitate is filtered and dried. The dried solid is then dissolved in hot water and the benzothiazole free base is liberated with saturated sodium bicarbonate solution. The white solid is collected by filtration and dried to give the crude product 24 which is used without further purification.

N,N'-Bis(2-disulfidyl-4-methoxyphenyl)-γ,γ'-diaminoisovaleric acid 25:

To a suspension of (1.0 g, 0.0022 mole) 24 in 40 mL distilled water is added (20.0 g, 0.357 mole) solid potassium hydroxide pellets and the resulting solution heated at 120° C. for 15–24 hours. The reaction mixture is then cooled in an ice bath and acidified with 5.0 N acetic acid to pH 5.0. The aqueous solution is extracted with three 100 mL portions of ethyl acetate and the combined ethyl acetate extracts are dried over anhydrous sodium sulfate and filtered. The filtrate is concentrated to dryness to give crude 25. The crude product is chromatographed on silica gel column using 20:80 mixture of ethyl acetate:hexane with 1% acetic acid as eluting solvent to give 25 as a crystalline yellow solid.

A magnetically stirred suspension of 1.0 g 25 in 100 mL absolute ethyl alcohol was saturated with dry hydrogen chloride gas. The resulting solution is then heated at reflux at 90° C. for two days. Upon cooling, the solvent is removed under reduced pressure and dried to give the crude product 26 as a dihydrochloride salt. The salt is dissolved in 50 ml distilled water and the pH of the resulting solution is adjusted to 8.5 to 9.0 with 0.2 M sodium bicarbonate solution. The aqueous solution is then extracted with three 100 mL portions of methylene chloride. The combined methylene chloride extracts are dried over anhydrous sodium sulfate and filtered. Solvent from the filtrate is removed under reduced pressure to give the crude product. The crude product is purified by silica gel chromatography eluting initially with methylene chloride and finally with ethyl acetate. The fractions containing the product are combined and concentrated to give 26.

Incorporation of a radionuclide metal into the chelating compound may be accomplished as described above in Example 1.

Ethyl-γ,γ'-di (p-methoxyanisidinyl) isovalerate 23:

A stirred solution of 7.5 g (70 mmole) 4-anisidine, 2.674 g (7 mmole) ethyl-3-iodomethyl-4-iodobutyrate 18 and 0.588 g (7 mmole) sodium bicarbonate in 30 mL dry dimethylsulfoxide is heated at 110° C. for 3 hours under nitrogen. The cooled mixture is then poured onto 400 mL ice-water with stirring. The resulting precipitate is collected by filtration and excess 4-anisidine in the precipitate is removed by washing with aqueous acetic acid. The product 23 is obtained by recrystallization of the washed precipitate in heptane.

Example 5

N,N'-Bis(2,2'-disulfidyl-4-methylphenyl-4'-succinimidyloxycarboxylphenyl)-1,3-propyldiamine

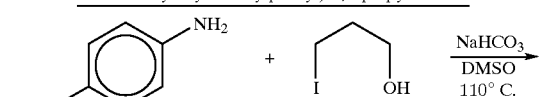

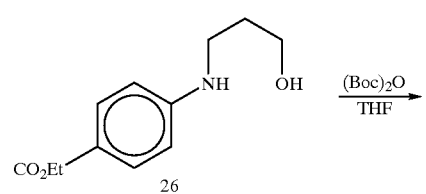

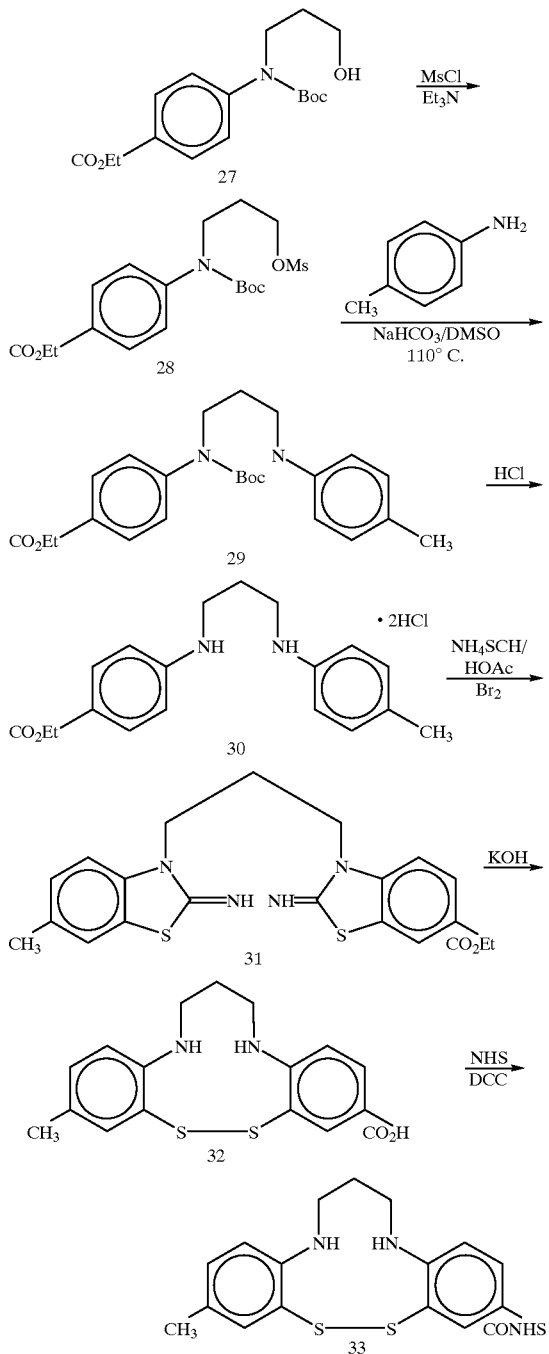

4-Ethyoxycarbonylanilino-3-propan-1-ol 26:

A stirred solution of 3-iodopropan-1-ol, sodium bicarbonate (1 equiv.) and ethyl-4-aminobenzoate (large excess) in dry dimethylsulfoxide (DMSO) is heated at 110° C. for 3 hours under nitrogen. Upon cooling, the mixture is poured into ice water with stirring and the resulting precipitate collected by filtration. The precipitate is then purified by silica gel chromatography (methylene chloride-methanol= 95:5 as the eluting solvent) to give the desired product, 26.

4-Ethyoxycarbonyl-N-Boc-anilino-3-propan-1-ol 27:

To a stirred solution of the p-ethoxycarbonylanilino-3-propan-1-ol, 26, in tetrahydrofuran (THF) is added 1 equiv. of di-t-butyl dicarbonate, (Boc)₂O. The reaction mixture is stirred overnight at room temperature. Solvent is removed under reduced pressure and the crude product is purified by silica gel chromatography (ethyl acetate as the eluting solvent) to give the product 27.

4-Ethyoxycarbonyl-N-Boc-anilino-3-propyl-1-oxy-1-O-mesylate 28:

To a solution of the p-ethyoxycarbonyl-N-Boc-anilino-3-propan-1-ol, 27, and triethylamine (1.1 equiv) in methylene chloride is added dropwise a solution of 1.1 equiv of mesylchloride in methylene chloride. The reaction mixture is stirred at room temperature under nitrogen overnight. Removal of solvent gives the crude product which is then purified by silica gel chromatography (ethyl acetate-hexane=1:1 as the eluting solvent) to give the product 28.

1-(4-Methylanilino)-3-(4-ethoxycarbonyl-N-Boc-anilino) propane 29:

A stirred solution of the 4-ethoxycarbonyl-N-Boc-anilino-3-propyl-1-oxy-1-O-mesylate, 28, sodium bicarbonate (1 equiv) and 4-aminotoluene (large excess) in dry DMSO is heated at 80° C. for 5 hours under nitrogen. Upon cooling, the mixture is poured into ice water with stirring and the resulting precipitate collected by filtration. The precipitate is washed with aqueous acetic acid until all of the excess amount of 4-aminotoluene is removed. The pure product is obtained after drying the washed precipitate under vacuum.

4-Methyl-4'-ethoxycarbonylpropyl-1,3-dianiline 30:

To a stirred solution of the 1-(4-methylanilino)-3-(4-ethoxycarbonyl-N-Boc-anilino)propane in dry dioxane is saturated with hydrogen chloride gas at 0° C. The reaction flask is sealed and stirred at room temperature for 14 hours. Solvent is removed under vacuum to give the product 30 as a colorless solid.

1,3-Di(2-imino-6-methyl-6'-ethyoxycarbonylbenzthiazolyl) propane 31:

Ammonium thiocyanate (16.5 g, 0.217 mole) is added to a magnetically stirred suspension of 30 (10.0 g, 0.03 moles) in 250 mL glacial acetic acid. A solution of bromine (34.6 g, 0.216 mole) in 50 mL acetic acid is then added dropwise to the suspension with stirring at room temperature. After stirring the reaction mixture overnight at room temperature, the dihydrobromide salt of the crude product is collected by filtration and dried. The product, 31, is isolated by dissolving the crude product in hot water, adjusting to basic pH with the addition of saturated sodium bicarbonate solution, collecting the precipitate by filtration, and drying in vitro.

N,N'-Bis(2,2'-disulfidyl-4-methylphenyl-4'-carboxylphenyl)-1,3-propyldiamine 32:

Solid potassium hydroxide (20.0 g, 0.357 mole) is added to a suspension of 31 (1.0 g, 0.0023 mole) in 40 mL distilled water, and the resulting mixture is heated at 120° C. for 24 hours. The reaction mixture is cooled in an ice bath and the pH is adjusted to 5.0 with 6.0 N acetic acid. The aqueous solution is then extracted with three 100 mL portions of ethyl acetate. The combined ethyl acetate extracts are dried over anhydrous sodium sulfate and the drying agent is removed. Removal of solvent yields 32.

N,N'-Bis(2,2'-disulfidyl-4-methylphenyl-4'-succinimidyloxycarboxylphenyl)-1,3-propyl-diamine 33:

Compound 32 is reacted with N-hydroxysuccinimide at room temperature using dicyclohexylcarbodiimide as a coupling reagent in either tetrahydrofuran (THF) or dimethylformamide (DMF) solvent. After stirring overnight at room temperature, removal of solvent provides the crude product which is then purified by silica gel chromatography to give compound 33.

Example 6

Propanedione bis(2-mercapto-4-ethoxycarbonylaniline technetium oxide

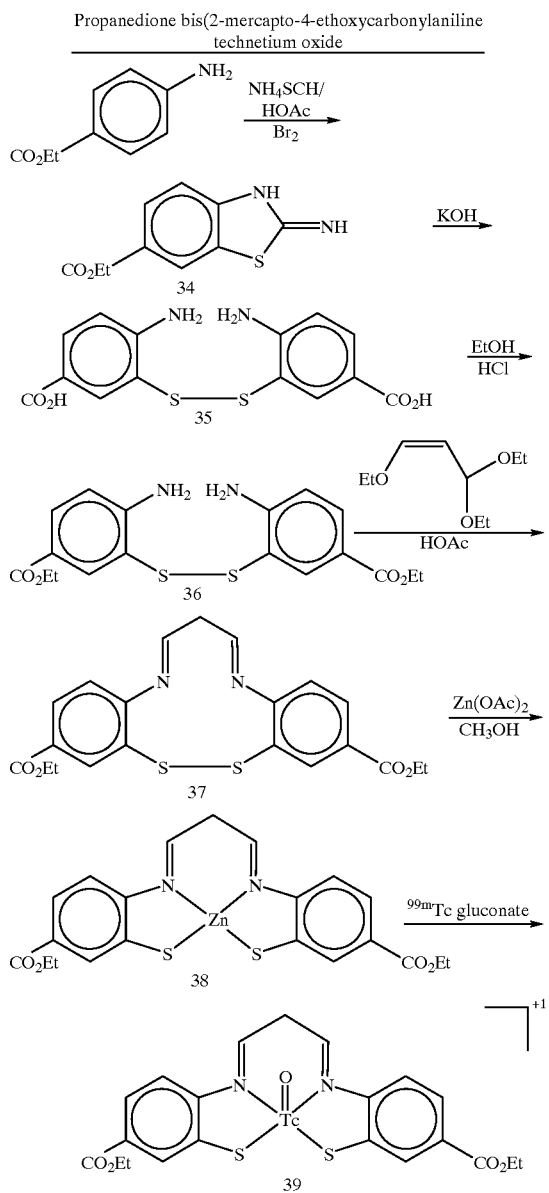

4'-Ethyoxycarbonyl-2-iminobenzthiazole 34:

Ammonium thiocyanate (6.9 g, 0.09 mole) is added to a magnetically stirred solution of ethyl 4-aminobenzoate, 5.0 g (0.03 moles) in 250 mL glacial acetic acid. A solution of bromine (14.5 g, 0.09 moles) in 50 mL glacial acetic acid is then added dropwise to the solution with stirring at room temperature. After stirring the reaction mixture overnight at room temperature, the hydrobromide salt of the crude product is collected by filtration and dried. The product, 34, is isolated by dissolving the crude product in hot water, adjusting it to basic pH with the addition of saturated sodium bicarbonate solution, collecting the precipitate by filtration and drying in vacuo.

5-carboxy-2-aminophenyldisulfide 35:

Solid potassium hydroxide (20.0 g, 0.357 mole) is added to a suspension of 34 (1.0 g, 0.005 mole) in 40 mL distilled water, and the resulting mixture is heated at 120° C. for 24 hours. The reaction mixture is then cooled in an ice bath and the pH is adjusted to 5.0 with 5.0 N acetic acid. The aqueous solution is then extracted with three 100 mL portions of ethyl acetate. The combined ethyl acetate extracts are dried over anhydrous sodium sulfate and the drying agent is filtered. Removal of solvent yields 5-carboxy-2-aminothiophenol which upon air oxidation yields the product, 5-carboxy-2-aminophenyldisulfide, 35.

5-Ethoxycarbonyl-2-aminophenyl disulfide 36:

To a stirred solution of the 5-carboxy-2-aminophenyl disulfide in absolute ethanol is saturated with HCl gas at 0° C. The reaction flask is sealed and the mixture is stirred at room temperature for three days. Solvent is removed under vacuum and the crude residue is purified by silica gel chromatography (methylene chloride and ethylacetate as the eluting solvent) to give the product 36.

N,N'-Bis(2-disulfidyl-4-ethoxycarbonylphenyl)-1,3-propyl diimine 37:

A stirred solution of the 5-ethoxycarbonyl-2-aminophenyl disulfide and β-ethoxy-acrolein-diethylacetal (prepared according to R. W. Price and A. Moosin, *J. Amer. Chem. Soc.* 67:207, 1945) in glacial acetic acid is heated in a boiling water bath for 5–10 min. The cooled reaction mixture is stored at 4° C. for one day. The resulting precipitate is collected by filtration and then recrystallized in aqueous ethanol to give the product 37.

Propanedione bis(2-mercapto-4-ethoxycarbonylaniline) zinc(II) 38:

To a refluxing solution of the N,N'-bis(2-disulfidyl-4-ethoxycarbonylphenyl)-1,3-propyl diimine, 37, in methanol is added a solution of zinc acetate in methanol under argon. The reaction mixture is heated at reflux for 30 min. Upon cooling the zinc complex is collected by filtration, washed with methanol and ether and dried under vacuum to give the product 38.

Propanedione bis(2-mercapto-4-ethoxycarbonylaniline) technetium oxide 39:

To a vial containing 0.1–1.0 mg 38, 0.1–1.0 mg stannous chloride dihydrate and lactose or mannitol (2.5–5.0 mg) at pH 5.0–7.0, is added 1.0 mL of sodium pertechnetate (100 mCi/mL). The reaction mixture is allowed to incubate at 100° C. for 15 minutes and provides 39 in good radiochemical yield and purity.

Example 7

N,N-Bis(2-disulfidyl-4-fluorophenyl)-a,b-diaminosuccinic anhydride

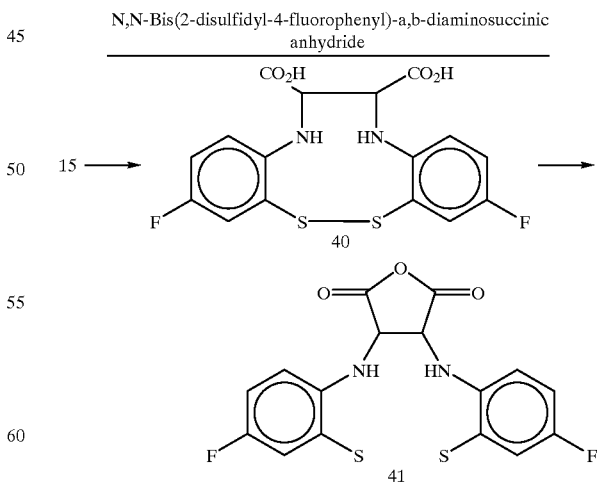

N,N'-Bis(2-disulfidyl-4-fluorophenyl)-α,β-diaminosuccinic acid 40:

Hydrolysis of diester 15 (prepared as described above in Example 2) by standard techniques provides diacid 40.

N,N'-Bis(2-disulfidyl-4-fluorophenyl)-α,β-diaminosuccinic anhydride 41:

To N,N'-bis(2-disulfidyl-4-fluorophenyl)-a,b-diaminosuccinic acid, 40, acetic anhydride or propionic anhydride is added and heated at 120° C.–130° C. for 26–48 hours. Removal of the solvent under reduced pressure gives the crude product which is then recrystallized from a polar/non polar aprotic solvent or sublimed to give N,N'-bis(2-disulfidyl-4-fluorophenyl)-α,β-diaminosuccinic anhydride, 41.

Example 8

Representative Synthesis of a Cyclic Chelating Compound

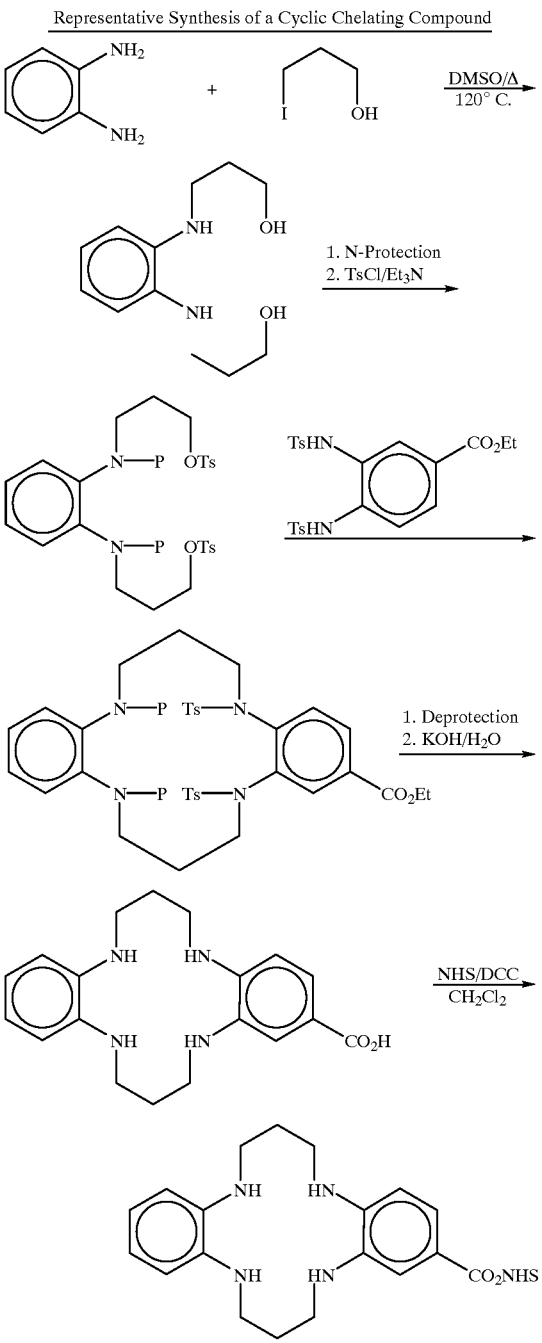

1,2-Phenylene diamine is reacted with excess 3-iodo-1-propanol in dimethylsulfoxide (DMSO) and like co-solvents at elevated temperatures (115–120° C.) to give a monosubstituted bis alcohol. The secondary amine functional groups are protected with t-Boc and/or similar functionalities followed by reaction with p-toluenesulfonyl chloride to give a bis tosylate. The tosylate is then added to a solution of 4-ethoxycarbonyl-1,2-phenylene tosyldiamide containing 2.1 equivalents of cesium carbonate in anhydrous tetrahydrofuran at low temperature. The reaction mixture is warmed up to room temperature and heated under reflux to yield a tetra amine protected cyclic adduct. Removal of the nitrogen protecting groups by known methods followed by ester hydrolysis yields a substituted tetra aza cyclam carboxylic acid derivative. Activation of the carboxylic acid to the succinimidate ester using a coupling agent such as dicyclohexylcarbodiimide (DCC) in an aprotic solvent affords an NHS ester of the substituted cyclam analog as a hydrochloride salt.

Example 9

Representative Synthesis of a Ketoester Chelating Compound

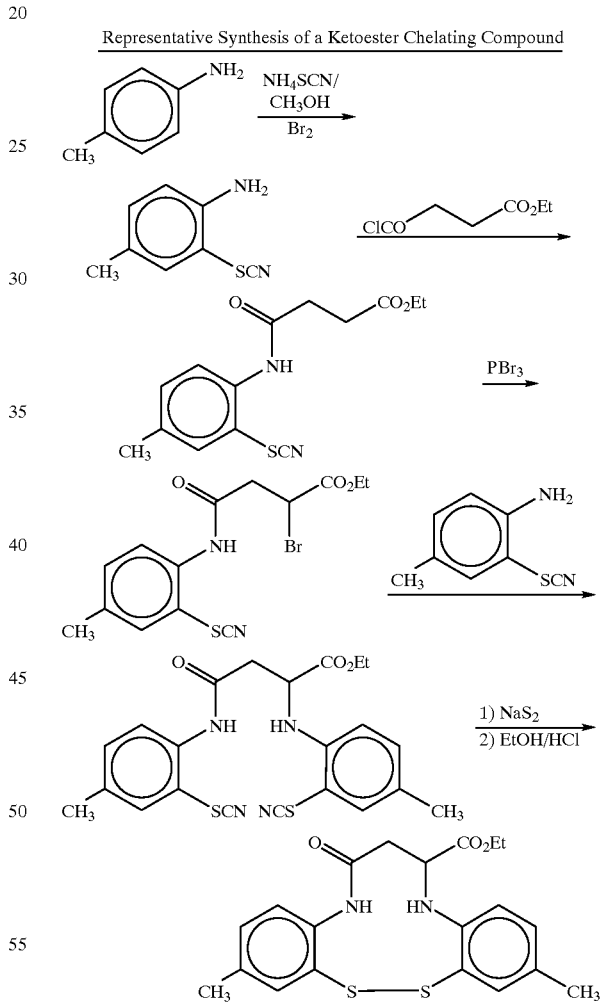

To a cooled, stirred solution of 4-toluidine and ammonium thiocyanate in methanol is added a solution of bromine in methanol. The reaction mixture is warmed to room temperature to give thiocyanate adduct. The amino thiocyanate is reacted with ethyl succinyl chloride under mild conditions to yield an ethyl hemisuccinamide derivative. Bromination at the methylene position with phosphorus tribromide gives a mono bromo ester. Displacement of bromide with 2-thiocyano-4-toluidine by heating in ethanol affords a secondary amine adduct. Hydrolysis of the thiocyanate to the thiol is carried out by heating in aqueous sodium disulfide followed by air oxidation to yield disulfide. Esterification of the carboxylic acid by treatment with ethanol in the presence of hydrogen chloride provides the ketoester. Incorporation of a radionuclide metal into the chelating compound may be accomplished as described in Example 1.

Example 10
Representative Preparation of a Metal Chelate Conjugate

Metal chelate conjugates are prepared from reactive chelating compounds (i.e., those with conjugation groups) and targeting moieties such as proteins. The following is a representative procedure for preparing metal chelate conjugates. In this example, chelating compound 33 is conjugated to annexin V, a placental anti-coagulant protein. The conjugate binds to activated platelets and is useful in visualizing blood clots.

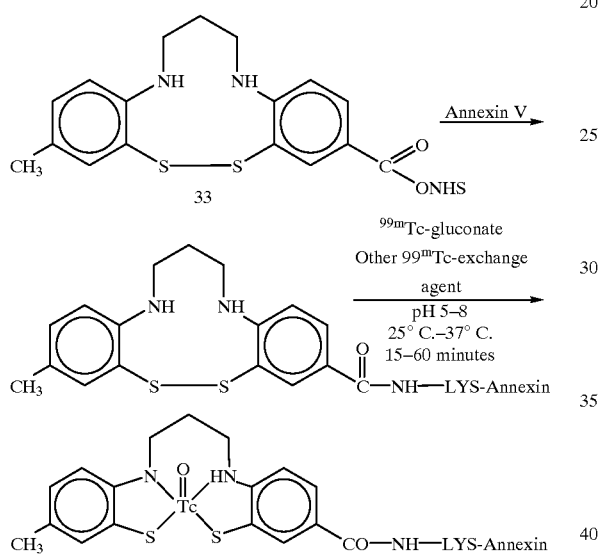

Conjugate preparation:

To a solution of 2.0 mg annexin-V (a targeting moiety) in 1.0 mL 0.2 M phosphate or bicarbonate buffer (pH 7.5–9.0) is added 50–100 µL of dimethylsulfoxide (DMSO) containing 130 µg (5 equivalents) compound 33 (prepared as described above in Example 5). The reaction mixture is carried out at room temperature for 15–30 minutes and purified either by dialysis or anion exchange chromatography. The purified post formed ligand-protein conjugate is lyophilized in phosphate buffered saline (PBS) containing 10% mannitol.

$^{99m}$Tc-radiolabeling:

Method A:

To a lyophilized 1–2 mg of post formed Annexin V conjugate prepared as described above is added 1.1 mL of Tc-99m gluconate (prepared from 0.12 mg stannous chloride dihydrate, 5.0 mg sodium gluconate at pH 6–7.5, and 100 mCi/mL of Tc-99m pertechnetate).

Method B:

Alternatively, a solution containing 0.12 mg stannous chloride dihydrate and 5.0 mg sodium gluconate at pH 6.0–7.5 are lyophilized along with the Annexin V conjugate containing mannitol. Metal chelation occurs upon addition of a solution of 1.0 mL of sodium pertechnetate (100 mCi/mL) to the lyophilized Annexin V conjugate.

In either of the above methods, the reaction mixture is incubated at 25° C.–37° C. for 15–60 minutes to complete the metallation. The Tc-99m radiolabeled Annexin V at a radiochemical purity of ≧80% as determined by an instant thin layer chromatography (ITLC) in 12% trichloroacetic acid (TCA) as a developing solvent.

Example 11

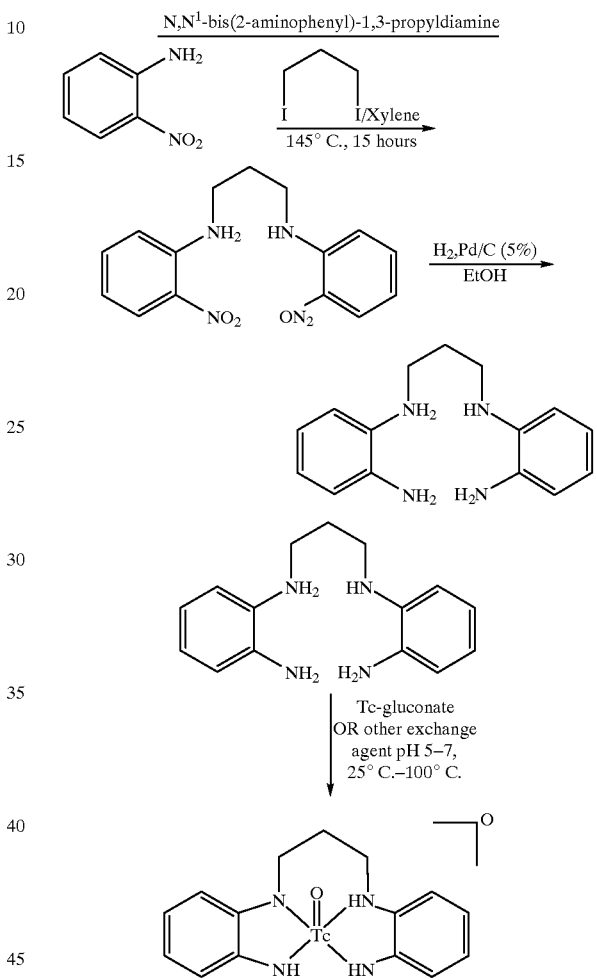

To a stirred suspension of 30.0 g (0.217 mole) 2-nitroaniline and 5.0 mL (0.044 mole) 1,3-diiodopropane in 100 mL xylene, 8.0 g (0.1 mole) solid sodium bicarbonate is added. The reaction mixture is heated at 145° C. for 15 hours under nitrogen. The progress of the reaction is monitored by silica gel thin layer chromatography. Solvent from the reaction mixture is removed under reduced pressure. The resulting crude product is purified by silica gel column chromatography. The product is eluted from the column initially with 20% Hexane in ethyl acetate and finally with 50% Hexane in ethyl acetate. The fractions containing the product are pooled and the solvent is removed under reduced pressure to yield the desired product.

N,N$^1$-bis(2-aminophenyl)-1,3-propyldiamine

To a solution of 1.0 g (0.003 mole) N,N$^1$-bis(2-nitrophenyl)-1,3-propyldiamine in 200 mL absolute alcohol is added 0.2 g of 5% palladium on activated carbon. The nitro function of the compound in the reaction mixture is reduced catalytically with H$_2$ gas in a pressure bottle at 60 PSI using Parr hydrogenation apparatus. The reduction is carried out for four hours and complete as indicated by no further consumption of $H_2$ gas. The reaction mixture is filtered and the solvent is removed under reduced pressure. To the crude residue a mixture of 30% hexane in ethyl acetate is added and the precipitate is filtered. Solvent from the filtrate is removed and the crude product is purified by silica gel column chromatography. The product is eluted with 50% Hexane ethyl acetate. The fractions containing the product are pooled and the solvent removed under reduced pressure to yield dry solid, $N,N^1$-bis(2-aminophenyl)-1,3-propyldiamine.

Tc-99m radiolabeling of $N,N^1$-bis (2-amino-phenyl)-1,3-Propyldiamine

A solution of 0.5 mL of 600 mg/mL $N,N^1$-bis (2-aminophenyl)-1,3-Propyldiamine in ethanol is added to 1.1 mL of Tc-99m gluconate (prepared from 0.12 mg stannous chloride dihydrate, 5.0 mg sodium gluconate at pH 6.1–6.3, and 100 mCi/mL of Tc-99m pertechnetate). The resulting mixture is incubated at room temperature for 15 minutes or heated at 75° C. for 5 minutes. The radiochemical purity of the product is $\geq$95% as analyzed by isocratic C-18 reverse phase high pressure liquid chromatography using 60% ethanol-saline as the mobile phase at a flow rate of 0.8 mL per minute.

Example 12

$N,N^1$-bis(2-hydroxylaminophenyl)-1,3-propyldiamine

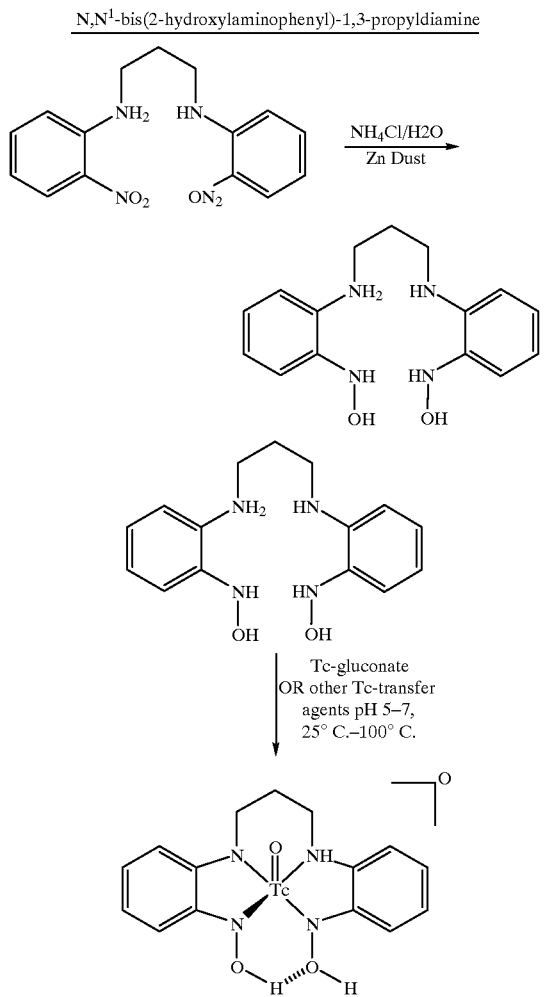

In a 100 mL round bottom flask are placed 0.40 g (0.008 molar) of ammonium chloride, 20 mL of water, and 1.0 g (0.003 mole) of $N,N^1$-bis(2-nitrophenyl)-1,3-propyldiamine.

The mixture is stirred vigorously by means of a magnetic stirrer, and 2.5 g of zinc dust is added during the course of 15 to 20 minutes. The reaction mixture is heated at 60° C. due to poor solubility of the nitro compound. Stirring is continued after all the zinc dust has been added, for an additional time period until disappearance of the starting compound by TLC. While still hot, the solution is filtered with suction in order to remove the zinc oxide, which is washed with additional 20 mL of hot water. The filtrate is cooled to −5° C. by being placed in an ice-salt mixture. The phenylhydroxlamine which crystallized out in light yellow flakes is filtered by suction and dried. The major product purified from the crude by silica gel column chromatography using 40% hexane-ethylacetate as eluting solvent is identified by NMR spectrometry to be over reduced compound $N,N^1$-bis (2-aminophenyl)-1,3-propyldiamine.

Tc-99m radiolabeling of $N,N^1$-bis (2-hydroxyl-aminophenyl)-1,3-prolyldiamine

A solution of 0.5 mL of 600 mg/mL $N,N^1$-bis(2-hydroxyl-aminophenyl)-1,3-propyldiamine in ethanol solution is added to 1.1 mL of Tc-99m gluconate (prepared from 0.12 mg stannous chloride dihydrate, 5.0 mg sodium gluconate at pH 6.1–6.3 and 100 mCi/mL of Tc-99m pertechnetate). The resulting reaction mixture is incubated at room temperature for 15 minutes or heated at 75° C. for 15 minutes. The radiochemical purity of the product is $\geq$80% as analyzed by isocratic C-18 reverse phase high pressure liquid chromatography using 60% ethanol-saline as the mobile phase at a flow rate of 0.8 mL per minute.

Example 13

$N,N^1$-bis(2-hydroxylaminophenyl)-1,3-propyldiamine

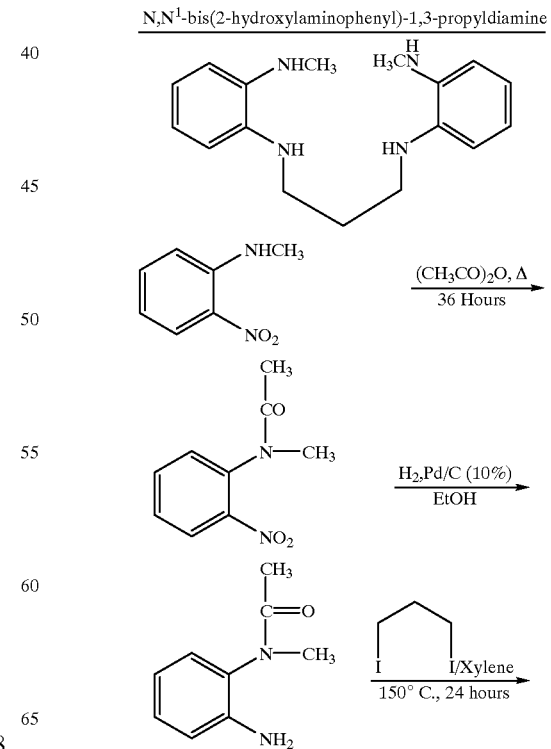

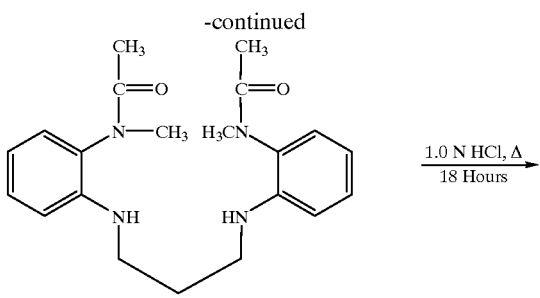

1.0 N HCl, Δ
18 Hours

N-Methyl 2-Nitro acetanilide

To 10.0 g (0.061 mole) of N-methyl 2-Nitro-aniline in a 250 mL round bottom flask, 100 mL of acetic anhydride is added. The reaction mixture is heated in an oil bath under reflux for 36 hours under anhydrous conditions. Solvent from the reaction mixture is removed under reduced pressure and dried. The crude product is purified by silica gel column chromatography. The crude product is loaded onto the silica gel column in methylene chloride solution. The product is initially eluted with 30% hexane-ethyl acetate and eventually with ethyl acetate. The fractions containing the product are pooled and the solvent removed under reduced pressure to yield the desired product.

N-Methyl 2-Amino acetanilide

To a solution of 5.0 g (0.026 moles) N-methyl 2-nitro acetanilide in 250 mL absolute alcohol is added 0.5 g of 10% palladium on activated carbon. The nitro functional group is reduced to amino functionality under catalytic reduction with hydrogen gas in a pressure bottle at 60 PSI using Parr hydrogenation apparatus. The reduction is carried out for five hours by which time the reaction is complete as indicated by no further consumption of $H_2$ gas. The reaction mixture is filtered and the solvent from the filtrate is removed under reduced pressure. To the crude residue a small amount of mixture of ethyl acetate ethanol is added and cooled. The resulting precipitate is filtered and washed with cold ethyl acetate in ethanol solvent and dried to give the desired compound N-methyl 2-amino acetanilide.

$N,N^1$-bis(2-(N-methyl N-acetyl) aminophenyl)-1,3-propyldiamine

To a stirred suspension of 3.0 g (0.018 moles) of N-methyl 2-amino acetanilide and 2.5 g (0.008 moles) of 1,3-diiodopropane in 100 mL xylene, 5.0 g (0.6 mole) of solid sodium bicarbonate is added. The reaction mixture is heated at 150° C. for 24 hours under nitrogen atmosphere. The progress of the reaction is monitored by thin layer chromatography in ethyl acetate developing solvent. After completion of reaction, solvent from the reaction mixture is removed under reduced pressure and dried. The resulting crude product is purified by silica gel column chromatography. Upon loading onto the column in methylene chloride solution, the crude product is initially eluted with 50% Hexane-ethyl acetate, followed by neat ethyl acetate solvent and finally with tetrahydrofuran solvent. The fractions containing the desired compound eluted following ethyl acetate and tetrahydrofuran elutions are combined. Solvent is removed under reduced pressure to yield a mixture of isomeric forms of the desired compound. The isomers are further separated in pure forms by another silica gel column chromatography upon loading the sample in methylene chloride and using ethyl acetate as an eluting solvent.

$N,N^1$-bis(2-methylaminophenyl)-1,3-propyl diamine

To 0.1 g (0.0003 mole) of white solid $N,N^1$-bis(2-(N-methyl N-acetyl) aminophenyl)-1,3-propyldiamine, 10.0 mL of 1.0 N hydrochloric acid solution is added. The suspension is heated at 90° C. under reflux for 24 hours. Solvent from the clear solution is removed under reduced pressure and dried to yield white solid as a hydrochloride salt. The white solid is basified with 0.2 M sodium bicarbonate solution. Solvent from the resulting basic solution is removed under reduced pressure and dried. To the dry pulverized white solid, anhydrous alcohol is added, stirred and filtered. The solvent from the filtrate is removed under reduced pressure. To the dry solid, 5 mL of methylene chloride is added, triturated and the light pink colored compound is filtered and dried to yield the desired $N,N^1$-bis(2-methylamino-phenyl)-1,3-propyldiamine.

Example 14

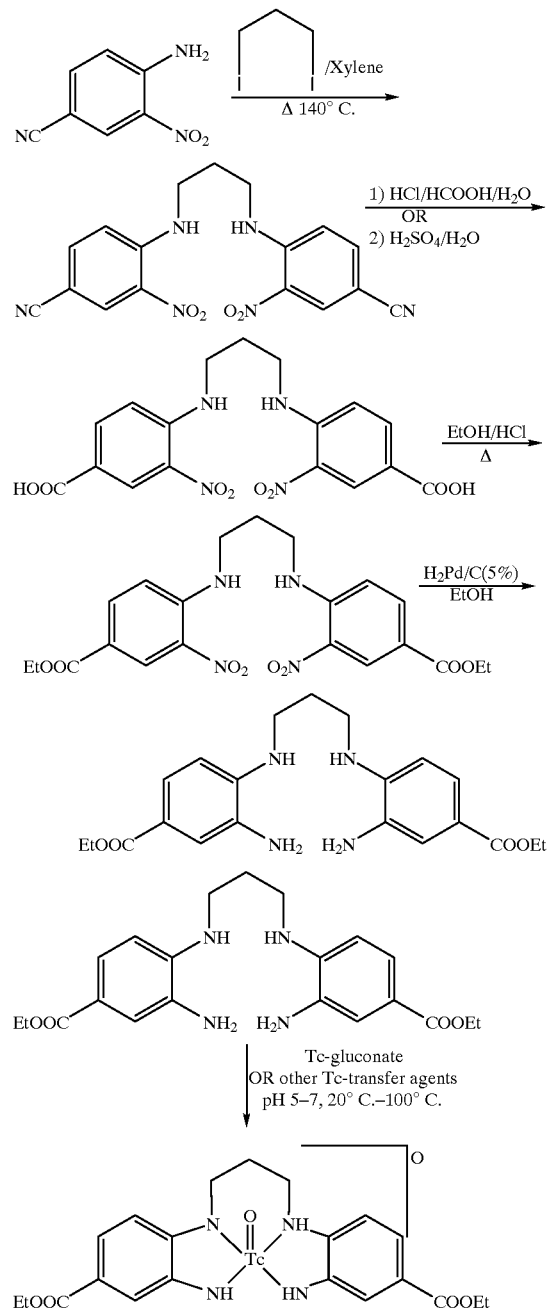

$N,N^1$-bis-(2-nitro-4-cyanophenyl)-1,3-propyldiamine

A stirred solution of 5.0 g (0.031 mole) 4-amino-3-nitrobenzonitrile, 35.0 mL (0.301 mole) 1,3-diiodopropane and 25.6 g (0.301 mole) solid sodium bicarbonate in 100 mL dry xylene is heated under reflux at 145° C. for 15–24 hours under nitrogen. The progress of the reaction is monitored by silica gel thin layer chromatography. Solvent from the reaction mixture is removed under reduced pressure in vacuo. The resulting crude product is purified by silica gel column chromatography using hexane/ethyl acetate solvent mixtures as elution solvent. Fractions containing the product are combined and solvent is removed under reduced pressure to yield the desired compound.

N,N¹-bis-(2-nitro-4-carboxyphenyl)-1,3-propyldiamine

A stirred suspension of 1.0 g (0.003 mole) N,N¹-bis-(2-nitro-4-cyanophenyl)-1,3-propyldiamine in aqueous hydrochloric acid-formic acid solution is heated under reflux. The progress of the reaction is monitored by silica gel thin layer chromatography. After completion of reaction, solvent is removed under vacuo to give N,N¹-bis-(2-nitro-4-carboxyphenyl)-1,3-propyldiamine. The crude product is further purified by either silica gel or reverse phase column chromatography.

N,N¹-bis-(2-nitro-4-ethoxycarbonylphenyl)-1,3-propyldiamine

A magnetically stirred suspension of N,N¹-bis-(2-nitro-4-carboxyphenyl)-1,3-propyldiamine (1.0 g, 0.0027 mole) in 200 mL absolute ethyl alcohol is saturated with dry hydrogen chloride gas. The reaction mixture is then heated under reflux for 24 hours. Upon cooling, solvent is removed under reduced pressure, to yield the desired product as its hydrochloride salt. A solution of the salt in 100 mL distilled water is adjusted to pH 8.5 to 9.0 with 0.2 M sodium bicarbonate solution and the aqueous solution extracted with three 100 mL portion methylene chloride. The combined methylene chloride extracts are dried over anhydrous sodium sulfate and the drying agent filtered. Removal of the solvent under reduced pressure gives the crude product which is purified and isolated by flash chromatography using silica gel and eluting with methylene chloride and ethyl acetate.

N,N¹-bis-(2-amino-4-ethoxycarbonylphenyl)-1,3-propyldiamine

To a solution of 5.0 g (0.011 mole) N,N¹-bis-(2-nitro-4-ethoxycarbonylphenyl)-1,3-propyldiamine in 200 mL absolute alcohol is added 0.5 g of 5% palladium on activated carbon. The nitro functional group is reduced to amino functionality under catalytic reduction with hydrogen gas in a pressure bottle at 60 PSI using Parr hydrogenation apparatus. The reduction is carried out for five hours by which time the reaction is complete as indicated by no further consumption of H₂ gas. The reaction mixture is filtered and the solvent from the filtrate is removed under reduced pressure. To the crude residue a small amount of a mixture of ethyl acetate and ethanol are added and cooled in ice. The resulting precipitate is filtered and washed with ethyl acetate and dried to give the desired compound N,N¹-bis-(2-amino-4-ethoxycarbonylphenyl)-1,3-propyldiamine.

Example 15

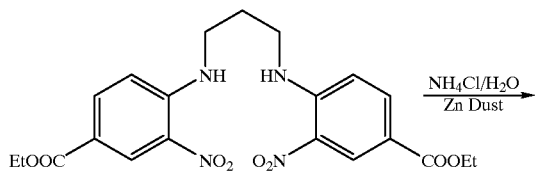

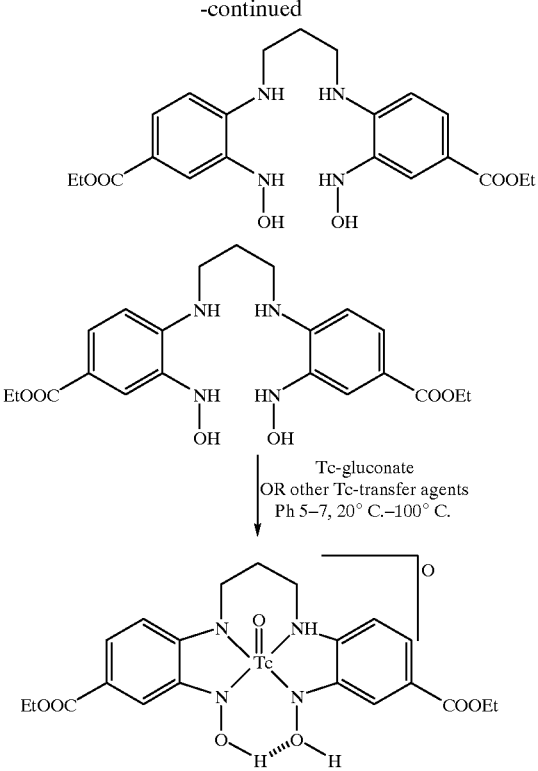

N,N¹-bis(2-hydroxylamino-4-ethoxycarbonylphenyl)-1,3-propyldiamine

In a 100 mL round bottom flask is placed 0.5 g (0.009 mole) of ammonium chloride, 20 mL water, and 1.0 g (0.002 mole) N,N¹-bis (2-nitro-4-ethoxycarbonylphenyl)-1,3-propyldiamine. The mixture is stirred vigorously by means of a magnetic stirrer and 2.5 g of zinc dust is added during the course of 15 to 20 minutes. The reaction mixture is warmed up to 60° C. Stirring is continued after all the zinc dust has been added, for an additional time period until disappearance of the starting compound by TLC. While still warm, the solution is filtered with suction in order to remove the zinc oxide, which is washed with an additional 20 mL of water. The filtrate is cooled to −5° C. by being placed in an ice salt mixture. The phenylhydroxylamine which crystallizes out in light yellow solid is filtered by suction and dried. Solvent from the filtrate is removed and the crude product is purified by flash chromatography on silica gel column using hexane-ethyl acetate mixture as an eluting solvent to give additional desired compound.

Tc-99m radiolabeling of N,N¹-bis(2-hydroxylamino-4-ethoxycarbonylphenyl)-1,3-propyldiamine A solution of 0.5 mL of 600 mg/mL N,N¹-bis(2-hydroxylamino-4-ethoxycarbonylphenyl)-1,3-propyldiamine in ethanol solution is added to 1.1 mL of Tc-99m gluconate (prepared from 0.12 mg stannous chloride dihydrate, 5.0 mg sodium gluconate at pH 6.1–6.3 and 100 mCi/mL of Tc-99m pertechnetate). The resulting reaction mixture is incubated at room temperature for 15 minutes or heated at 75° C. for 15 minutes. The radiochemical purity of the product is ≧95% as analyzed by isocratic C-18 reverse phase high pressure liquid chromatography using 60% ethanol-saline as the mobile phase at a flow rate of 0.8 mL per minute.

Example 16

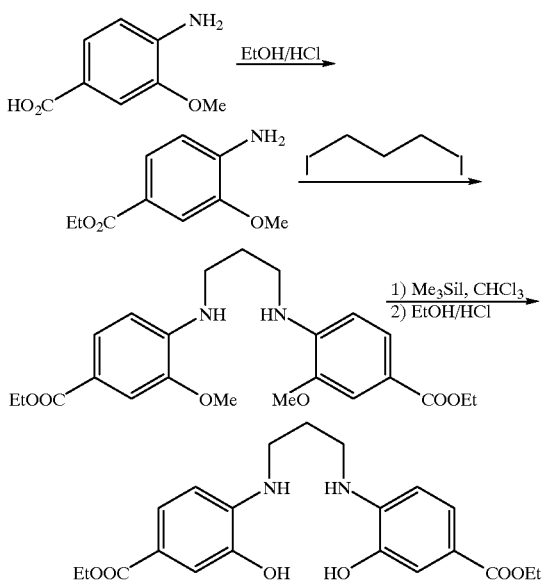

Ethyl-4-amino-3-methoxybenzoate

To a solution of 3.343 g (20 mmole) of 4-amino-3-methoxybenzoic acid in 200 mL EtOH is bubbled a stream of HCl gas for three minutes. The HCl saturated solution is stirred at room temperature for two days. Solvent is evaporated under vacuum and the resulting residue is dissolved in 100 mL water. The water layer is basified with $K_2CO_3$ and extracted with $CH_2Cl_2$ (3×200 mL). The combined $CH_2Cl_2$ layer is washed with saturated $NaHCO_3$ (200 mL), brine and then dried over $MgSO_4$, filtered and evaporated under reduced pressure to give the desired product.

N,N$^1$-bis (4-ethoxycarbonyl-2-methoxyphenyl)-1,3-propyldiamine

A stirred solution of 3.514 g (18 mmole) of ethyl-4-amino-3-methoxybenzoate, 207 mL (1.8 mmole) of 1,3-diiodopropane and 151 mg (1.8 mmole) of sodium bicarbonate in 10 mL dry DMSO is heated at 110° C. for three hours under nitrogen. Upon cooling, the mixture is poured into 200 mL ice water with stirring and the resulting precipitate collected by filtration. This crude precipitate is purified by silica gel chromatography eluting with $CH_2Cl_2$/MeOH (98/2) to provide the desired product.

N,N$^1$-bis (4-ethoxycarbonyl-2-hydroxyphenyl)-1,3-propyldiamine

To a stirred solution of 235 mg (1 mmole) of N,N$^1$-bis (4-ethoxycarbonyl-2-methoxyphenyl)-1,3-propyldiamine in 10 mL chloroform is added 0.85 mL (1.2 g;6 mmole) of iodotrimethylsilane. The reaction mixture is stirred at room temperature for 48 hours. Solvent is removed under reduced pressure and the resulting residue is dissolved in 30 mL EtOH. To this EtOH solution is bubbled a stream of HCl gas for three minutes. The HCl saturated solution is stirred at room temperature for 48 hours. Solvent is removed under reduced pressure to give a crude product. This crude product is purified by HPLC on a preparative C-18 column eluting with increase gradient of MeOH in water to provide the desired product as the HCl salt form.

From the foregoing, it will be appreciated that, although specific embodiments of the invention have been described herein for purposes of illustration, various modifications may be made without deviating from the spirit and scope of the invention.

We claim:

1. A compound of the formula:

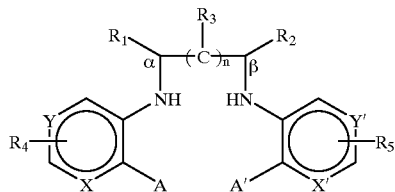

wherein:

n=0 or 1;

$R_1$ and $R_2$ are independently selected from the group consisting of hydrogen, =O with the proviso that both are not =O, $-(CH_2)_m Z$ where m is 0–10 and Z represents a conjugation group or targeting moiety, and $-(CH_2)_m W$ where m is 0–10 and W represents a hydrolyzable group, or $R_1$ and $R_2$ are taken together to form a cyclic anhydride or a benzene ring, wherein the conjugation group is an anhydride or active ester, the targeting moiety is a protein or biotin, and the hydrolyzable group is an imidate, ester or carbamate;

$R_3$ is selected from the group consisting of hydrogen, lower alkyl, substituted lower alkyl, alkoxy, perhaloalkyl, halogen, hydroxyl, nitro, $-(CH_2)_m Z$, and $-(CH_2)_m W$;

$R_4$ and $R_5$ are attached at one or more of the ring positions and are independently selected from the group consisting of hydrogen, lower alkyl, substituted lower alkyl, alkoxy, perhaloalkyl, halogen, hydroxyl, nitro, $-(CH_2)_m Z$, and $-(CH_2)_m W$;

A and A' are independently selected from the group consisting of nitrogen and sulfur, where a sulfur may bear a hydrogen or a sulfur protecting group, or where A and A' are both sulfur, A and A' may be joined together by a bond, and where a nitrogen may bear a hydrogen, a hydroxyl or a lower alkyl substituent, or where A and A' are both nitrogen, A and A' may be joined by $-CH_2-(CH_2)_n-CH_2-$ where n is 0 or 1;

X, Y, X' and Y' are independently selected from the group consisting of carbon and nitrogen;

α and β represent carbon atoms which may bear a carbon-nitrogen double bond; and said compound has at least one Z or W.

2. The compound of claim 1 wherein:

$R_1$ and $R_2$ are independently selected from the group consisting of hydrogen, =O with the proviso that both are not =O, $-(CH_2)_m Z$ where m is 0–10 and Z represents a conjugation group or targeting moiety according to claim 1, or $R_1$ and $R_2$ are taken together to form a cyclic anhydride or a benzene ring;

$R_3$ is selected from the group consisting of hydrogen, lower alkyl, substituted lower alkyl, alkoxy, perhaloalkyl, halogen, hydroxyl, nitro, and $-(CH_2)_m Z$;

$R_4$ and $R_5$ are attached at one or more of the ring positions and are independently selected from the group consisting of hydrogen, lower alkyl, substituted lower alkyl, alkoxy, perhaloalkyl, halogen, hydroxyl, nitro, and $-(CH_2)_m Z$; and said compound has at least one Z.

3. The compound of claim 2 wherein n=1; $R_1$, $R_2$ and $R_3$ are hydrogen; $R_4$ and $R_5$ are independently selected from the group consisting of hydrogen and $-(CH_2)_m Z$ where m=0, with the proviso that at least one is -(CH$_2$)$_m$Z; A and A' are both sulfur, optionally joined together by a bond; and X, Y, X' and Y' are carbon.

4. The compound of claim 2 wherein R$_1$ and R$_2$ are taken together to form a cyclic anhydride; n=0; R$_4$ and R$_5$ are fluorine; A and A' are both sulfur, optionally joined together by a bond; and X, Y, X' and Y' are carbon.

5. The compound of claim 2 wherein n=1; R$_1$ and R$_2$ are hydrogen; R$_3$ is -(CH$_2$)$_m$Z where m=0; R$_4$ and R$_5$ are fluorine; A and A' are both sulfur, optionally joined together by a bond; and X, Y, X' and Y' are carbon.

6. The compound of claim 1 wherein:

R$_1$ and R$_2$ are independently selected from hydrogen, =O with the proviso that both are not =O, -(CH$_2$)$_m$W where m is 0–10 and W represents a hydrolyzable group according to claim 1, or R$_1$ and R$_2$ are taken together to form a benzene ring;

R$_3$ is hydrogen, lower alkyl, substituted lower alkyl, alkoxy, perhaloalkyl, halogen, hydroxyl, nitro, and -(CH$_2$)$_m$W;

R$_4$ and R$_5$ are attached at one or more of the ring positions and are independently selected from hydrogen, lower alkyl, substituted lower alkyl, alkoxy, perhaloalkyl, halogen, hydroxyl, nitro, and -(CH$_2$)$_m$W; and said compound has at least one W.

7. The compound of claim 6 wherein R$_1$ and R$_2$ are independently selected from the group consisting of hydrogen, =O with the proviso that both are not =O, or -(CH$_2$)$_m$W; R$_3$ is hydrogen or -(CH$_2$)$_m$W; R$_4$ and R$_5$ are -(CH$_2$)$_m$W; A and A' are both sulfur, optionally joined together by a bond; X, Y, X' and Y' are carbon.

8. The compound of claim 6 wherein n=1; R$_1$, R$_2$ and R$_3$ are hydrogen; R$_4$ and R$_5$ are -(CH$_2$)$_m$W; A and A' are both sulfur, optionally joined together by a bond; and X, Y, X' and Y' are carbon.

9. The compound of claim 6 wherein n=0; R$_1$ and R$_2$ are -(CH$_2$)$_m$W; R$_4$ and R$_5$ are fluorine; A and A' are both sulfur, optionally joined together by a bond; and X, Y, X' and Y' are carbon.

10. The compound of claim 6 wherein n=1; R$_1$ is =O and R$_2$ is -(CH$_2$)$_m$W; R$_3$ is hydrogen; R$_4$ and R$_5$ are fluorine; A and A' are both sulfur, optionally joined together by a bond; and X, Y, X' and Y' are carbon.

11. The compound of claim 6 wherein n=1; R$_1$, R$_2$ and R$_3$ are hydrogen; R$_4$ and R$_5$ are chlorine; A and A' are both sulfur, optionally joined together by a bond; and X and X' are carbon, and Y and Y' are nitrogen.

12. The compound of claim 1 wherein:

R$_1$ and R$_2$ are independently selected from hydrogen or -(CH$_2$)$_m$W where m is 0–10 and W represents a hydrolyzable group according to claim 1;

R$_3$ is hydrogen, lower alkyl, substituted lower alkyl, alkoxy, perhaloalkyl, halogen, hydroxyl, nitro, and -(CH$_2$)$_m$W;

R$_4$ and R$_5$ are attached at one or more of the ring positions and are independently selected from hydrogen, lower alkyl, substituted lower alkyl, alkoxy, perhaloalkyl, halogen, hydroxyl, nitro, and -(CH$_2$)$_m$W; and said compound has at least one W.

13. The compound of claim wherein n=1; R$_1$, R$_2$, and R$_3$ are hydrogen; R$_4$ and R$_5$ are -(CH$_2$)$_m$W; A and A' are both sulfur, optionally joined together by a bond; and X, Y, X' and Y' are carbon.

14. A complex comprising a compound according to any one of claims 1, 2, 3, 4, 5, 6, 7, 9, 10, 11, 12 or 13, with a radionuclide metal or an oxide or a nitride thereof.

15. A complex according to claim 14, wherein said radionuclide is a radionuclide of technetium, copper, rhenium, lead, bismuth, ruthenium, rhodium, gold or palladium.

16. A complex of the formula:

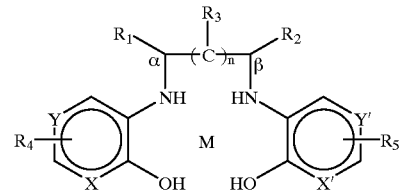

wherein:

n=0 or 1;

R$_1$ and R$_2$ are independently selected from hydrogen, =O with the proviso that both are not =O, -(CH$_2$)$_m$Z where m is 0–10 and Z represents a conjugation group or targeting moiety, and -(CH$_2$)$_m$W where m is 0–10 and W represents a hydrolyzable group, or R$_1$ and R$_2$ are taken together to form a cyclic anhydride or a benzene ring, wherein the conjugation group is an anhydride or active ester, the targeting moiety is a protein or biotin, and the hydrolyzable group is an imidate, ester or carbamate;

R$_3$ is hydrogen, lower alkyl, substituted lower alkyl, alkoxy, perhaloalkyl, halogen, hydroxyl, nitro, -(CH$_2$)$_m$Z, and -(CH$_2$)$_m$W;

R$_4$ and R$_5$ are attached at one or more of the ring positions and are independently selected from hydrogen, lower alkyl, substituted lower alkyl, alkoxy, perhaloalkyl, halogen, hydroxyl, nitro, -(CH$_2$)$_m$Z, and -(CH$_2$)$_m$W;

M is a radionuclide metal or an oxide or a nitride thereof;

X, Y, X' and Y' are independently selected from carbon and nitrogen;

α and β represent carbon atoms which may bear a carbon-nitrogen double bond; and said complex has at least one Z or W.

* * * * *

UNITED STATES PATENT AND TRADEMARK OFFICE
CERTIFICATE OF CORRECTION

PATENT NO. : 6,024,937
DATED : Feb. 15, 2000
INVENTOR(S) : Sudhakar Kasina, Eric Yau, and John M. Reno It is certified that error appears in the above-identified patent and that said Letters Patent is hereby corrected as shown below:

Claim 6, column 43, line 23, "and arc independently" should read --and are independently--.

Claim 12, column 44, line 2, "and arc independently" should read --and are independently--.

Claim 14, column 44, line 11, "1,2,3,4,5,6,7,9,10,11,12 or 13" should read -- 1,2,3,4,5,6,7,8,9,10,11,12 or 13--.

In the last line of the abstract, "$^{186188}$Re." should read --$^{186/188}$Re.--.

Signed and Sealed this

Twentieth Day of February, 2001

Attest:

NICHOLAS P. GODICI

Attesting Officer    Acting Director of the United States Patent and Trademark Office